US012070082B2

United States Patent
Garris et al.

(10) Patent No.: US 12,070,082 B2
(45) Date of Patent: *Aug. 27, 2024

(54) DEVICE AND SYSTEM FOR VALIDATION AND MODIFICATION OF DEVICE STATE TRANSITIONS FOR AN AEROSOL GENERATION DEVICE

(71) Applicant: RAI STRATEGIC HOLDINGS, INC., Winston-Salem, NC (US)

(72) Inventors: Robert Logan Garris, Winston-Salem, NC (US); Sean Lukan, Winston-Salem, NC (US); Jim Marting, Winston-Salem, NC (US); Sean Daugherty, Winston-Salem, NC (US); Austin Carpenter, Winston-Salem, NC (US); Spencer Mougey, Winston-Salem, NC (US); Keith Anderson, Winston-Salem, NC (US)

(73) Assignee: RAI STRATEGIC HOLDINGS, INC., Winston-Salem, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/125,505

(22) Filed: Mar. 23, 2023

(65) Prior Publication Data

US 2023/0225422 A1 Jul. 20, 2023

Related U.S. Application Data

(63) Continuation of application No. 17/313,051, filed on May 6, 2021, now Pat. No. 11,641,885.

(51) Int. Cl.
*A24F 40/80* (2020.01)
*A24F 40/53* (2020.01)
(Continued)

(52) U.S. Cl.
CPC .............. *A24F 40/80* (2020.01); *A24F 40/53* (2020.01); *G01M 99/005* (2013.01); *G06F 11/26* (2013.01); *A61M 15/06* (2013.01)

(58) Field of Classification Search
None
See application file for complete search history.

(56) References Cited

U.S. PATENT DOCUMENTS

2013/0255702 A1* 10/2013 Griffith, Jr. ............. A24F 15/01
131/328
2016/0363570 A1 12/2016 Blackley
(Continued)

FOREIGN PATENT DOCUMENTS

| KR | 1020180105662 | 9/2018 |
| WO | 2016079533 | 5/2016 |
| WO | 2021034555 | 2/2021 |

OTHER PUBLICATIONS

International Search Report and Written Opinion of corresponding International Application No. PCT/US2022/027981 mailed Sep. 13, 2022.

*Primary Examiner* — Raul J Rios Russo
*Assistant Examiner* — Carl F. R. Tchatchouang
(74) *Attorney, Agent, or Firm* — BURR & FORMAN LLP

(57) ABSTRACT

A test fixture for testing aerosol provision devices may include a housing, a plurality of testing modules disposed at the housing where each of the testing modules includes a cavity configured to receive a portion of an aerosol provision device, and processing circuitry operably coupled to the testing modules. Each of the testing modules may be configured to interface with an assembly of a respective one of the aerosol provision devices to transition the assembly between an initial state and a transitioned state during a functional test controlled by the processing circuitry. The (Continued)

processing circuitry may be configured to conduct the functional test of at least two of the testing modules simultaneously.

18 Claims, 9 Drawing Sheets

(51) Int. Cl.
*A61M 15/06* (2006.01)
*G01M 99/00* (2011.01)
*G06F 11/26* (2006.01)

(56) References Cited

U.S. PATENT DOCUMENTS

| | | |
|---|---|---|
| 2020/0187560 A1 | 6/2020 | Trzecieski |
| 2020/0315259 A1 | 10/2020 | Hubbard et al. |
| 2022/0232902 A1 | 7/2022 | Batista et al. |
| 2022/0256929 A1 | 8/2022 | Jacobs, Jr. et al. |
| 2022/0346447 A1 | 11/2022 | Hupkes |

* cited by examiner

DEVICE AND SYSTEM FOR VALIDATION AND MODIFICATION OF DEVICE STATE TRANSITIONS FOR AN AEROSOL GENERATION DEVICE

CROSS-REFERENCE TO RELATED APPLICATIONS

The present application is a continuation of U.S. application Ser. No. 17/313,051 filed May 6, 2021, which is incorporated by reference herein in its entirety.

TECHNICAL FIELD

Example embodiments generally relate to non-combustible aerosol provision systems and, in particular, relate to a device and system for testing and confirming the capability of an aerosol provision device to conduct post sale activation (PSA).

BACKGROUND

Non-combustible aerosol provision systems (e.g., e-cigarettes/tobacco heating products or other such devices) generally contain an aerosolisable material, such as a reservoir of a source liquid containing a formulation. The formulation typically includes nicotine, or a solid material such as a tobacco-based product, from which an aerosol is generated for inhalation by a user, for example through heat vaporization. However, devices including formulations with other materials, such as cannabinoids (e.g., Tetrahydrocannabinol (THC) and/or Cannabidiol (CBD)), botanicals, medicinals, caffeine, and/or other active ingredients, are also possible. Thus, a non-combustible aerosol provision system will typically include an aerosol generation chamber containing a vaporizer, e.g., a heater, arranged to vaporize a portion of the aerosolisable material to generate an aerosol in the aerosol generation chamber. As a user inhales on a mouthpiece of the device and electrical power is supplied to the heater, air is drawn into the device and into the aerosol generation chamber where the air mixes with the vaporized aerosolisable material and forms a condensation aerosol. There is a flow path between the aerosol generation chamber and an opening in the mouthpiece so the air drawn through the aerosol generation chamber continues along the flow path to an opening in the mouthpiece, carrying some of the condensation aerosol with it, and out through the opening in the mouthpiece for inhalation by the user.

Aerosol provision systems include, for example, vapor products, such as those delivering nicotine that are commonly known as "electronic cigarettes," "e-cigarettes" or electronic nicotine delivery systems (ENDS), as well as heat-not-burn products including tobacco heating products (THPs). Many of these products take the form of a system including a device and a consumable, and it is the consumable that includes the material from which the substance to be delivered originates. Typically, the device is reusable, and the consumable is single-use (although some consumables are refillable as in the case of so called "open" systems). Therefore, in many cases, the consumable is sold separately from the device, and often in a multipack. Moreover, subsystems and some individual components of devices or consumables may be sourced from specialist manufacturers.

Aerosol provision devices, like those described above, may be subject to certain restrictions, including age restrictions. In some locations, use of the articles including the cartridges of an ENDS device is limited based on user age. To accommodate the need for authentication of a device by an age verified user, any of a number of authentication methods may be employed. However, many of these authentication methods may require interaction with a host device (e.g., a smartphone or other wireless communication device that can access authentication services). These authentication methods may therefore rely on the ability of the user to effectively carry on the interaction between the host device and the aerosol provision device in order to seamlessly complete the authentication process. Accordingly, it may be desirable to introduce methods, devices or systems that ensure the reliability of the aerosol provision devices relative to their proper setup for PSA, and ensure that they also have the proper functional capability to be authenticated by authorized or age verified users.

BRIEF SUMMARY OF SOME EXAMPLES

In an example embodiment, a test fixture for testing aerosol provision devices with respect to proper unlocking of such devices in connection with a PSA process be provided. The test fixture may include a housing, a plurality of testing modules disposed at the housing where each of the testing modules includes a cavity configured to receive a portion of an aerosol provision device, and processing circuitry operably coupled to the testing modules. Each of the testing modules may be configured to interface with an assembly of a respective one of the aerosol provision devices to transition the assembly between an initial and a transitioned state during a functional test controlled by the processing circuitry. The processing circuitry may be configured to conduct the functional test of at least two of the testing modules simultaneously.

It will be appreciated that this Brief Summary is provided merely for purposes of summarizing some example implementations to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying drawings which illustrate, by way of example, the principles of some described example implementations.

BRIEF DESCRIPTION OF THE SEVERAL VIEWS OF THE DRAWING(S)

Having thus described some example embodiments in general terms, reference will now be made to the accompanying drawings, which are not necessarily drawn to scale, and wherein:

DETAILED DESCRIPTION

Figure 1A:
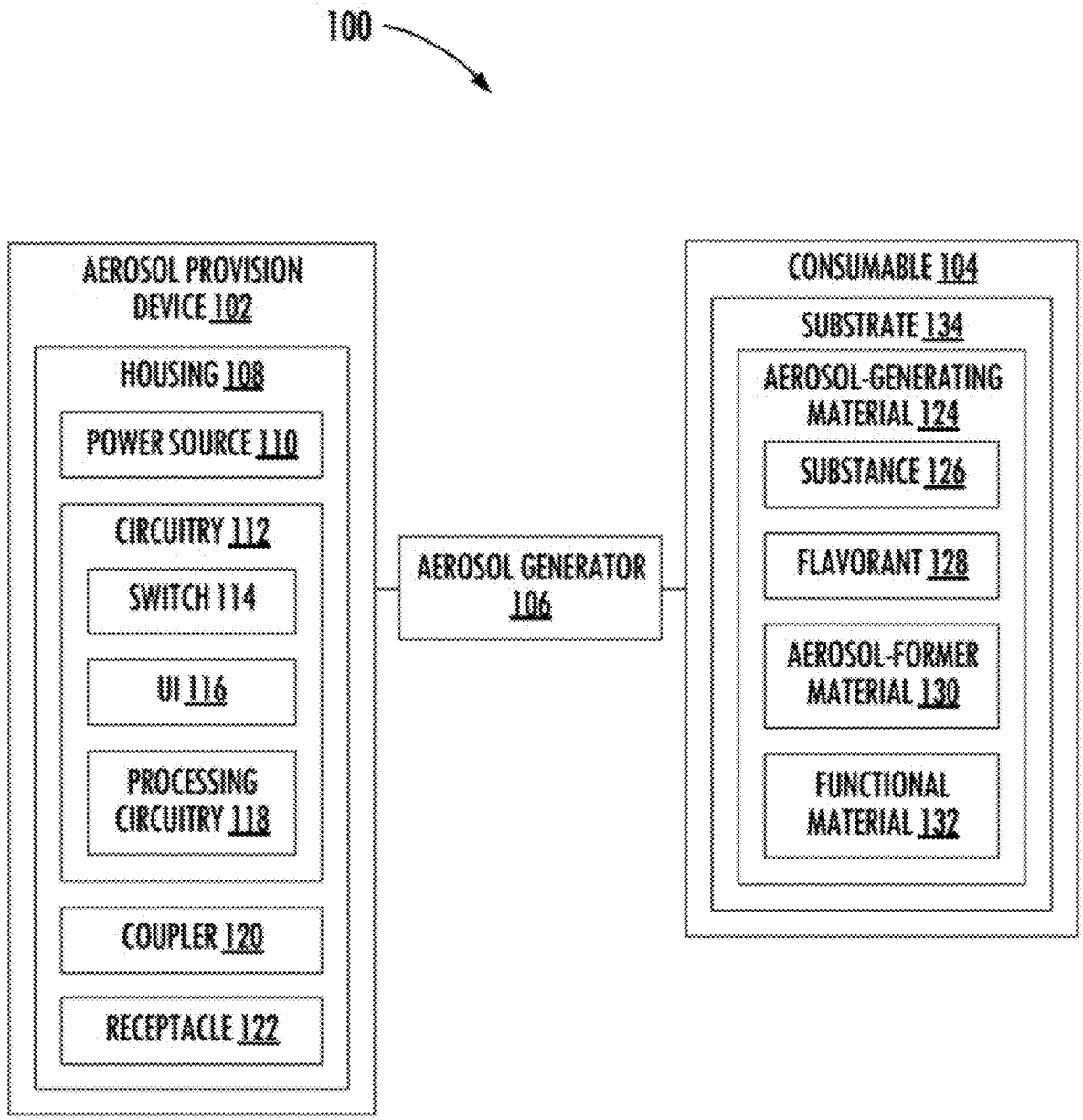
FIG. 1A illustrates a general block diagram of a non-combustible aerosol provision system that may be used in connection with an example embodiment.

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout. As used herein, operable coupling should be understood to relate to direct or indirect connection that, in either case, enables functional interconnection of components that are operably coupled to each other.

As indicated above, the present disclosure relates to requiring an authentication of an age-restricted device, such as an aerosol delivery device or an electronic nicotine delivery systems ("ENDS") device. The authentication may include or require a prior age verification, such that the age-restricted device is not operational for a user that is not age-verified. The authentication may include the age-restricted device receiving a control signal for authenticating the device. The control signal may include audio signals and/or visual/optical signals for authenticating the device. In some case, the authentication may be initiated after a device wakeup procedure, in order to conserve power prior to authentication. However, in any case, the authentication (and/or wakeup) may be initiated by insertion of a dedicated module into the device. The module may therefore be added to minimize changes to existing ENDS device designs.

An aerosol delivery device or ENDS is one example of a device that may be associated with restriction, such as an age restriction. Other examples include delivery devices for delivery of cannabinoids, such as Tetrahydrocannabinol (THC) and/or Cannabidiol (CBD), botanicals, medicinals, and/or other active ingredients. Thus, it will be appreciated that while an aerosol delivery or ENDS device is used as an example application of various embodiments throughout, this example is intended to be non-limiting such that inventive concepts disclosed herein can be used with devices other than aerosol delivery or ENDS devices, including aerosol delivery devices that may be used to deliver other medicinal and/or active ingredients to a user or may include smokeless tobacco or other tobacco products.

The device authentication by a control signal can be in addition to, or may be required as a prerequisite to, the user performing age verification. A user that has not been age verified cannot authenticate a device. The authentication may need to be performed periodically for usage of an age-restricted product. There may be an age verification system for confirming an age of a user and/or authenticating the proper user and/or device. In any case, these activities may be referred to generally as post sale activation (PSA).

The conduct of PSA is generally well received by consumers as long as the procedures for conducting PSA are relatively straightforward to employ. That said, if consumers encounter technical problems with any degree of frequency in the performance of PSA, negative impacts on brand loyalty and overall product usage can be expected. Thus, it may be desirable to confirm, prior to shipping of aerosol delivery devices for distribution, that each such device can be properly locked and unlocked. Example embodiments may provide a test fixture and/or methods for ensuring that aerosol delivery devices are functionally equipped to be locked and unlocked in association with PSA.

Given that example embodiments may be employed in connection with providing security for non-combustible aerosol provision systems such as ENDS devices, a general description of an example device will be provided since some aspects of the test fixture may be tailored to interface with the case and/or other structural aspects of the ENDS devices.

Unless specified otherwise or clear from context, references to first, second or the like should not be construed to imply a particular order. A feature described as being above another feature (unless specified otherwise or clear from context) may instead be below, and vice versa; and similarly, features described as being to the left of another feature else may instead be to the right, and vice versa. Also, while reference may be made herein to quantitative measures, values, geometric relationships or the like, unless otherwise stated, any one or more if not all of these may be absolute or approximate to account for acceptable variations that may occur, such as those due to engineering tolerances or the like.

As used herein, unless specified otherwise or clear from context, the "or" of a set of operands is the "inclusive or" and thereby true if and only if one or more of the operands is true, as opposed to the "exclusive or" which is false when all of the operands are true. Thus, for example, "[A] or [B]" is true if [A] is true, or if [B] is true, or if both [A] and [B] are true. Further, the articles "a" and "an" mean "one or more," unless specified otherwise or clear from context to be directed to a singular form. Furthermore, it should be understood that unless otherwise specified, the terms "data," "content," "digital content," "information," and similar terms may be at times used interchangeably.

Example implementations of the present disclosure are generally directed to test fixtures or methods for interfacing with delivery systems designed to deliver at least one substance to a user, such as to satisfy a particular "consumer moment." The substance may include constituents that impart a physiological effect on the user, a sensorial effect on the user, or both.

Delivery systems may take many forms. Examples of suitable delivery systems include aerosol provision systems such as powered aerosol provision systems designed to release one or more substances or compounds from an aerosol-generating material without combusting the aerosol-generating material. These aerosol provision systems may at times be referred to as non-combustible aerosol provision systems, aerosol delivery devices or the like, and the aerosol-generating material may be, for example, in the form of a solid, semi-solid, liquid or gel and may or may not contain nicotine.

Examples of suitable aerosol provision systems include vapor products, heat-not-burn products, hybrid products and the like. Vapor products are commonly known as "electronic cigarettes," "e-cigarettes" or electronic nicotine delivery systems (ENDS), although the aerosol-generating material need not include nicotine. Many vapor products are designed to heat a liquid material to generate an aerosol. Other vapor products are designed to break up an aerosol-generating material into an aerosol without heating, or with only secondary heating. Heat-not-burn products include tobacco heating products (THPs) and carbon-tipped tobacco heating products (CTHPs), and many are designed to heat a solid material to generate an aerosol without combusting the material.

Hybrid products use a combination of aerosol-generating materials, one or a plurality of which may be heated. Each of the aerosol-generating materials may be, for example, in the form of a solid, semi-solid, liquid, or gel. Some hybrid products are similar to vapor products except that the aerosol generated from a liquid or gel aerosol-generating material passes through a second material (such as tobacco) to pick up additional constituents before reaching the user. In some example implementations, the hybrid system includes a liquid or gel aerosol-generating material, and a solid aerosol-generating material. The solid aerosol-generating material may include, for example, tobacco or a non-tobacco product.

FIG. 1A is a block diagram of an aerosol provision system 100 according to some example implementations. In various examples, the aerosol provision system may be a vapor product, heat-not-burn product or hybrid product. The aerosol provision system includes one or more of each of a number of components including, for example, an aerosol provision device 102, and a consumable 104 (sometimes referred to as an article) for use with the aerosol provision device. The aerosol provision system also includes an aerosol generator 106. In various implementations, the aerosol generator may be part of the aerosol provision device or the consumable. In other implementations, the aerosol generator may be separate from the aerosol provision device and the consumable, and removably engaged with the aerosol provision device and/or the consumable.

In various examples, the aerosol provision system 100 and its components including the aerosol provision device 102 and the consumable 104 may be reusable or single-use. In some examples, the aerosol provision system including both the aerosol provision device and the consumable may be single use. In some examples, the aerosol provision device may be reusable, and the consumable may be reusable (e.g., refillable) or single use (e.g., replaceable). In yet further examples, the consumable may be both refillable and also replaceable. In examples in which the aerosol generator 106 is part of the aerosol provision device or the consumable, the aerosol generator may be reusable or single-use in the same manner as the aerosol provision device or the consumable.

In some example implementations, the aerosol provision device 102 may include a housing 108 with a power source 110 and circuitry 112. The power source is configured to provide a source of power to the aerosol provision device and thereby the aerosol provision system 100. The power source may be or include, for example, an electric power source such as a non-rechargeable battery or a rechargeable battery, solid-state battery (SSB), lithium-ion battery, supercapacitor, or the like.

The circuitry 112 may be configured to enable one or more functionalities (at times referred to as services) of the aerosol provision device 102 and thereby the aerosol provision system 100. The circuitry includes electronic components, and in some examples one or more of the electronic components may be formed as a circuit board such as a printed circuit board (PCB).

In some examples, the circuitry 112 includes at least one switch 114 that may be directly or indirectly manipulated by a user to activate the aerosol provision device 102 and thereby the aerosol provision system 100. The switch may be or include a pushbutton, touch-sensitive surface or the like that may be operated manually by a user. Additionally or alternatively, the switch may be or include a sensor configured to sense one or more process variables that indicate use of the aerosol provision device or aerosol provision system. One example is a flow sensor, pressure sensor, pressure switch or the like that is configured to detect airflow or a change in pressure caused by airflow when a user draws on the consumable 104.

The switch 114 may provide user interface functionality. In some examples, the circuitry 112 may include a user interface (UI) 116 that is separate from or that is or includes the switch. The UI may include one or more input devices and/or output devices to enable interaction between the user and the aerosol provision device 102. As described above with respect to the switch, examples of suitable input devices include pushbuttons, touch-sensitive surfaces and the like. The one or more output devices generally include devices configured to provide information in a human-perceptible form that may be visual, audible or tactile/haptic. Examples of suitable output devices include light sources such as light-emitting diodes (LEDs), quantum dot-based LEDs and the like. Other examples of suitable output devices include display devices (e.g., electronic visual displays), touchscreens (integrated touch-sensitive surface and display device), loudspeakers, vibration motors and the like.

In some examples, the circuitry 112 includes processing circuitry 118 configured to perform data processing, application execution, or other processing, control or management services according to one or more example implementations. The processing circuitry may include a processor embodied in a variety of forms such as at least one processor core, microprocessor, coprocessor, controller, microcontroller or various other computing or processing devices including one or more integrated circuits such as, for example, an ASIC (application specific integrated circuit), an FPGA (field programmable gate array), some combination thereof, or the like. In some examples, the processing circuitry may include memory coupled to or integrated with the processor, and which may store data, computer program instructions executable by the processor, some combination thereof, or the like.

As also shown, in some examples, the housing 108 and thereby the aerosol provision device 102 may also include a coupler 120 and/or a receptacle 122 structured to engage and hold the consumable 104, and thereby couple the aerosol provision device with the consumable. The coupler may be or include a connector, fastener or the like that is configured to connect with a corresponding coupler of the consumable, such as by a press fit (or interference fit) connection, threaded connection, magnetic connection or the like. The receptacle may be or include a reservoir, tank, container, cavity, receiving chamber or the like that is structured to receive and contain the consumable or at least a portion of the consumable.

The consumable 104 is an article including aerosol-generating material 124 (also referred to as an aerosol precursor composition), part or all of which is intended to be consumed during use by a user. The aerosol provision system 100 may include one or more consumables, and each consumable may include one or more aerosol-generating materials. In some examples in which the aerosol provision system is a hybrid product, the aerosol provision system may include a liquid or gel aerosol-generating material to generate an aerosol, which may then pass through a second, solid aerosol-generating material to pick up additional constituents before reaching the user. These aerosol-generating materials may be within a single consumable or respective consumables that may be separately removable.

The aerosol-generating material 124 is capable of generating aerosol, for example when heated, irradiated or energized in any other way. The aerosol-generating material may be, for example, in the form of a solid, semi-solid, liquid or gel. The aerosol-generating material may include an "amorphous solid," which may be alternatively referred to as a "monolithic solid" (i.e., non-fibrous). In some examples, the amorphous solid may be a dried gel. The amorphous solid is a solid material that may retain some fluid, such as liquid, within it. In some examples, the aerosol-generating material may include from about 50 wt %, 60 wt % or 70 wt % of amorphous solid, to about 90 wt %, 95 wt % or 100 wt % of amorphous solid.

The aerosol-generating material 124 may include one or more of each of a number of constituents such as an active substance 126, flavorant 128, aerosol-former material 130 or other functional material 132.

The active substance 126 may be a physiologically active material, which is a material intended to achieve or enhance a physiological response such as improved alertness, improved focus, increased energy, increased stamina, increased calm or improved sleep. The active substance may for example be selected from nutraceuticals, nootropics, psychoactives. The active substance may be naturally occurring or synthetically obtained. The active substance may include, for example, nicotine, caffeine, GABA (γ-aminobutyric acid), L-theanine, taurine, theine, vitamins such as B6 or B12 (cobalamin) or C, melatonin, cannabinoids, terpenes, or constituents, derivatives, or combinations thereof. The active substance may include one or more constituents, derivatives or extracts of tobacco, cannabis or another botanical.

In some examples in which the active substance 126 includes derivatives or extracts, the active substance may be or include one or more cannabinoids or terpenes.

As noted herein, the active substance 126 may include or be derived from one or more botanicals or constituents, derivatives or extracts thereof. As used herein, the term "botanical" includes any material derived from plants including, but not limited to, extracts, leaves, bark, fibers, stems, roots, seeds, flowers, fruits, pollen, husk, shells or the like. Alternatively, the material may include an active compound naturally existing in a botanical, obtained synthetically. The material may be in the form of liquid, gas, solid, powder, dust, crushed particles, granules, pellets, shreds, strips, sheets, or the like. Example botanicals are tobacco, eucalyptus, star anise, hemp, cocoa, cannabis, fennel, lemongrass, peppermint, spearmint, rooibos, chamomile, flax, ginger, ginkgo biloba, hazel, hibiscus, laurel, licorice (liquorice), matcha, mate, orange skin, papaya, rose, sage, tea such as green tea or black tea, thyme, clove, cinnamon, coffee, aniseed (anise), basil, bay leaves, cardamom, coriander, cumin, nutmeg, oregano, paprika, rosemary, saffron, lavender, lemon peel, mint, juniper, elderflower, vanilla, wintergreen, beefsteak plant, curcuma, turmeric, sandalwood, cilantro, bergamot, orange blossom, myrtle, cassis, valerian, pimento, mace, damien, marjoram, olive, lemon balm, lemon basil, chive, carvi, verbena, tarragon, geranium, mulberry, ginseng, theanine, theacrine, maca, ashwagandha, damiana, guarana, chlorophyll, baobab or any combination thereof. The mint may be chosen from the following mint varieties: Mentha arventis, Mentha c.v., Mentha niliaca, Mentha piperita, Mentha piperita citrata c.v., Mentha piperita c.v, Mentha spicata crispa, Mentha cardifolia, Mentha longifolia, Mentha suaveolens variegata, Mentha pulegium, Mentha spicata c.v. and Mentha suaveolens.

In yet other examples, the active substance 126 may be or include one or more of 5-hydroxytryptophan (5-HTP)/oxitriptan/Griffonia simplicifolia, acetylcholine, arachidonic acid (AA, omega-6), ashwagandha (Withania somnifera), Bacopa monniera, beta alanine, beta-hydroxy-beta-methylbutyrate (HMB), Centella asiatica, chai-hu, cinnamon, citicoline, cotinine, creatine, curcumin, docosahexaenoic acid (DHA, omega-3), dopamine, Dorstenia arifolia, Dorstenia Odorata, essential oils, GABA, Galphimia glauca, glutamic acid, hops, kaempferia parviflora (Thai ginseng), kava, L-carnitine, L-arginine, lavender oil, L-choline, liquorice, L-lysine, L-theanine, L-tryptophan, lutein, magnesium, magnesium L-threonate, myo-inositol, nardostachys chinensis, nitrate, oil-based extract of Viola odorata, oxygen, phenylalanine, phosphatidylserine, quercetin, resveratrol, Rhizoma gastrodiae, Rhodiola, Rhodiola rosea, rose essential oil, S-adenosylmethionine (SAMe), sceletium tortuosum, schisandra, selenium, serotonin, skullcap, spearmint extract, spikenard, theobromine, tumaric, Turnera aphrodisiaca, tyrosine, vitamin A, vitamin B3, or yerba mate.

In some example implementations, the aerosol-generating material 124 includes a flavorant 128. As used herein, the terms "flavorant" and "flavor" refer to materials which, where local regulations permit, may be used to create a desired taste, aroma or other somatosensorial sensation in a product for adult consumers. Flavorants may include naturally occurring flavor materials, botanicals, extracts of botanicals, synthetically obtained materials, or combinations thereof (e.g., tobacco, cannabis, licorice (liquorice), hydrangea, eugenol, Japanese white bark magnolia leaf, chamomile, fenugreek, clove, maple, matcha, menthol, Japanese mint, aniseed (anise), cinnamon, turmeric, Indian spices, Asian spices, herb, wintergreen, cherry, berry, redberry, cranberry, peach, apple, orange, mango, clementine, lemon, lime, tropical fruit, papaya, rhubarb, grape, durian, dragon fruit, cucumber, blueberry, mulberry, citrus fruits, Drambuie, bourbon, scotch, whiskey, gin, tequila, rum, spearmint, peppermint, lavender, aloe vera, cardamom, celery, cascarilla, nutmeg, sandalwood, bergamot, geranium, khat, naswar, betel, shisha, pine, honey essence, rose oil, vanilla, lemon oil, orange oil, orange blossom, cherry blossom, cassia, caraway, cognac, jasmine, ylang-ylang, sage, fennel, wasabi, piment, ginger, coriander, coffee, hemp, a mint oil from any species of the genus Mentha, eucalyptus, star anise, cocoa, lemongrass, rooibos, flax, ginkgo biloba, hazel, hibiscus, laurel, mate, orange skin, rose, tea such as green tea or black tea, thyme, juniper, elderflower, basil, bay leaves, cumin, oregano, paprika, rosemary, saffron, lemon peel, mint, beefsteak plant, curcuma, cilantro, myrtle, cassis, valerian, pimento, mace, damien, marjoram, olive, lemon balm, lemon basil, chive, carvi, verbena, tarragon, limonene, thymol, camphene), flavor enhancers, bitterness receptor site blockers, sensorial receptor site activators or stimulators, sugars and/or sugar substitutes (e.g., sucralose, acesulfame potassium, aspartame, saccharine, cyclamates, lactose, sucrose, glucose, fructose, sorbitol, or mannitol), and other additives such as charcoal, chlorophyll, minerals, botanicals, or breath freshening agents. Flavorants may be imitation, synthetic or natural ingredients or blends thereof. Flavorants may be in any suitable form, for example, liquid such as an oil, solid such as a powder, or gas.

In some example implementations, the flavorant 128 may include a sensate, which is intended to achieve a somatosensorial sensation which are usually chemically induced and perceived by the stimulation of the fifth cranial nerve (trigeminal nerve), in addition to or in place of aroma or taste nerves, and these may include agents providing heating, cooling, tingling, numbing effect. A suitable heat effect agent may be, but is not limited to, vanillyl ethyl ether and a suitable cooling agent may be, but not limited to eucolyptol, WS-3.

The aerosol-former material 130 may include one or more constituents capable of forming an aerosol. In some example implementations, the aerosol-former material may include one or more of glycerine, glycerol, propylene glycol, diethylene glycol, triethylene glycol, tetraethylene glycol, 1,3-butylene glycol, erythritol, meso-Erythritol, ethyl vanillate, ethyl laurate, a diethyl suberate, triethyl citrate, triacetin, a diacetin mixture, benzyl benzoate, benzyl phenyl acetate, tributyrin, lauryl acetate, lauric acid, myristic acid, and propylene carbonate.

The one or more other functional materials 132 may include one or more of pH regulators, colouring agents, preservatives, binders, fillers, stabilizers, and/or antioxidants. Suitable binders include, for example, pectin, guar gum, fruit pectin, citrus pectin, tobacco pectin, hydroxyethyl guar gum, hydroxypropyl guar gum, hydroxyethyl locust bean gum, hydroxypropyl locust bean gum, alginate, starch, modified starch, derivatized starch, methyl cellulose, ethyl cellulose, ethylhydroxymethyl cellulose, carboxymethyl cellulose, tamarind gum, dextran, pullalon, konjac flour or xanthan gum.

In some example implementations, the aerosol-generating material 124 may be present on or in a support to form a substrate 134. The support may be or include, for example, paper, card, paperboard, cardboard, reconstituted material (e.g., a material formed from reconstituted plant material, such as reconstituted tobacco, reconstituted hemp, etc.), a plastics material, a ceramic material, a composite material, glass, a metal, or a metal alloy. In some examples, the support includes a susceptor, which may be embedded within the aerosol-generating material, or on one or either side of the aerosol-generating material.

Although not separately shown, in some example implementations, the consumable 104 may further include receptacle structured to engage and hold the aerosol-generating material 124, or substrate 134 with the aerosol-generating material. The receptacle may be or include a reservoir, tank, container, cavity, receiving chamber or the like that is structured to receive and contain the aerosol-generating material or the substrate. The consumable may include an aerosol-generating material transfer component (also referred to as a liquid transport element) configured to transport aerosol-generating material to the aerosol generator 106. The aerosol-generating material transfer component may be adapted to wick or otherwise transport aerosol-generating material via capillary action. In some examples, the aerosol-generating material transfer component may include a microfluidic chip, a micro pump or other suitable component to transport aerosol-generating material.

The aerosol generator 106 (also referred to as an atomizer, aerosolizer or aerosol production component) is configured to energize the aerosol-generating material 124 to generate an aerosol, or otherwise cause generation of an aerosol from the aerosol-generating material. More particularly, in some examples, the aerosol generator may be powered by the power source 110 under control of the circuitry 112 to energize the aerosol-generating material to generate an aerosol.

In some example implementations, the aerosol generator 106 is an electric heater configured to perform electric heating in which electrical energy from the power source is converted to heat energy, which the aerosol-generating material is subject to so as to release one or more volatiles from the aerosol-generating material to form an aerosol. Examples of suitable forms of electric heating include resistance (Joule) heating, induction heating, dielectric and microwave heating, radiant heating, arc heating and the like. More particular examples of suitable electric heaters include resistive heating elements such as wire coils, flat plates, prongs, micro heaters or the like.

In some example implementations, the aerosol generator 106 is configured to cause an aerosol to be generated from the aerosol-generating material without heating, or with only secondary heating. For example, the aerosol generator may be configured to subject the aerosol-generating material to one or more of increased pressure, vibration, or electrostatic energy. More particular examples of these aerosol generators include jet nebulizers, ultrasonic wave nebulizers, vibrating mesh technology (VMT) nebulizers, surface acoustic wave (SAW) nebulizers, and the like.

A jet nebulizer is configured to use compressed gas (e.g., air, oxygen) to break up aerosol-generating material 124 into an aerosol, and an ultrasonic wave nebulizer is configured to use ultrasonic waves to break up aerosol-generating material into an aerosol. A VMT nebulizer includes a mesh, and a piezo material (e.g., piezoelectric material, piezomagnetic material) that may be driven to vibrate and cause the mesh to break up aerosol-generating material into an aerosol. A SAW nebulizer is configured to use surface acoustic waves or Rayleigh waves to break up aerosol-generating material into an aerosol.

In some examples, the aerosol generator 106 may include a susceptor, or the susceptor may be part of the substrate 134. The susceptor is a material that is heatable by penetration with a varying magnetic field generated by a magnetic field generator that may be separate from or part of the aerosol generator. The susceptor may be an electrically-conductive material, so that penetration thereof with a varying magnetic field causes induction heating of the heating material. The heating material may be magnetic material, so that penetration thereof with a varying magnetic field causes magnetic hysteresis heating of the heating material. The susceptor in some examples may be both electrically-conductive and magnetic, so that the susceptor of these examples is heatable by both heating mechanisms.

Although not separately shown, either or both the aerosol provision device 102 or the consumable 104 may include an aerosol-modifying agent. The aerosol-modifying agent is a substance configured to modify the aerosol generated from the aerosol-generating material 124, such as by changing the taste, flavor, acidity or another characteristic of the aerosol. In various examples, the aerosol-modifying agent may be an additive or a sorbent. The aerosol-modifying agent may include, for example, one or more of a flavorant, colorant, water or carbon adsorbent. The aerosol-modifying agent may be a solid, semi-solid, liquid or gel. The aerosol-modifying agent may be in powder, thread or granule form. The aerosol-modifying agent may be free from filtration material. In some examples, the aerosol-modifying agent may be provided in an aerosol-modifying agent release component, that is operable to selectively release the aerosol-modifying agent.

The aerosol provision system 100 and its components including the aerosol provision device 102, consumable 104, and aerosol generator 106 may be manufactured with any of a number of different form factors, and with additional or alternative components relative to those described above.

Figure 1B:
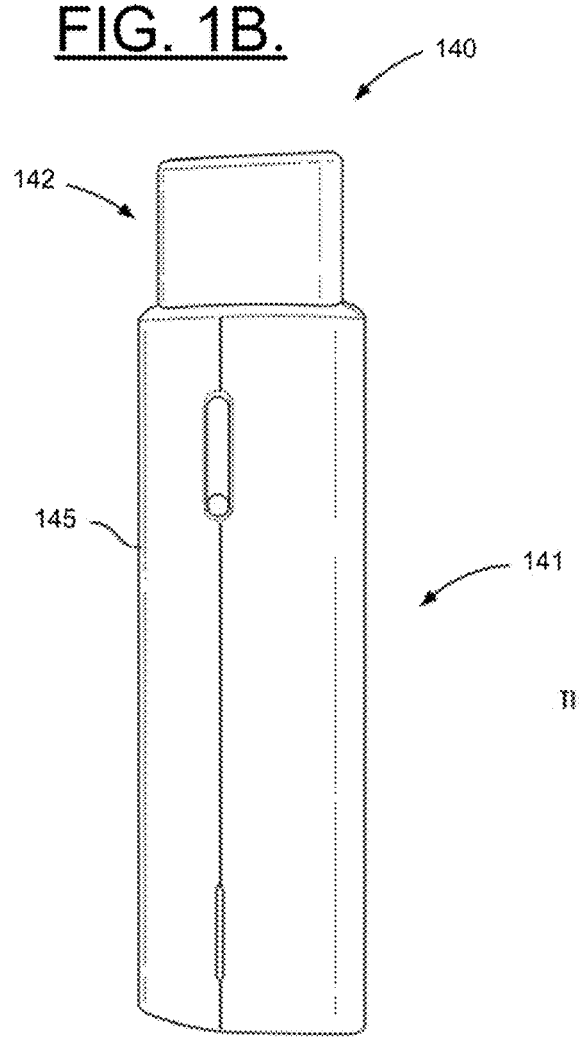
FIGS. 1B and 1C illustrate an aerosol provision system in the form of a vapor product, according to some example implementations.
Figure 1C:
Figure 1C:
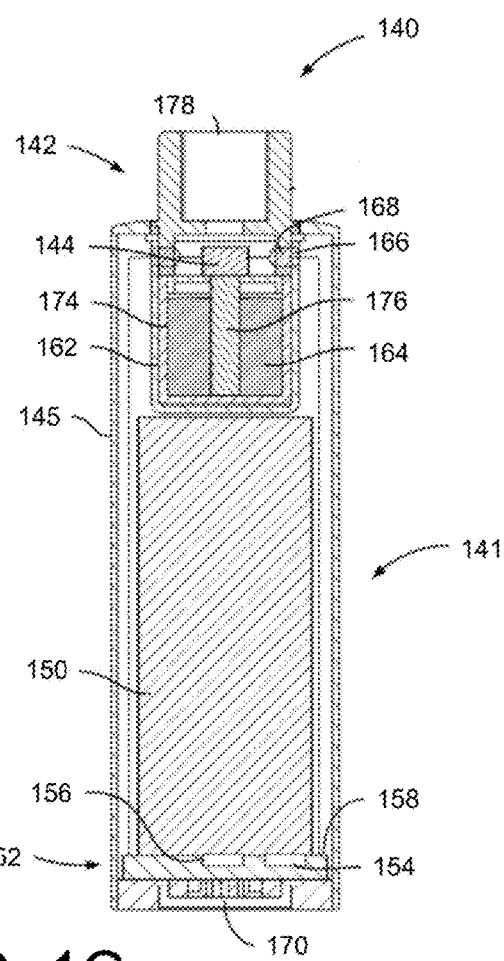

FIGS. 1B and 1C illustrate an aerosol provision system 140 in the form of a vapor product, and that in some example implementations may correspond to the aerosol provision system 100. As shown, the aerosol provision system 140 may include an aerosol provision device 141 (also referred to as a control body or power unit) and a consumable 142 (also referred to as a cartridge or tank), which may correspond to respectively the aerosol provision device 102 and the consumable 104. The aerosol provision system and in particular the consumable may also include an aerosol generator corresponding to the aerosol generator 106, and in the form of an electric heater 144 such as a heating element like a metal plate or metal wire coil configured to convert electrical energy to heat energy through resistance (Joule) heating. The aerosol provision device and the consumable can be permanently or detachably aligned in a functioning relationship. FIGS. 1B and 1C illustrate respectively a perspective view and a partially cut-away side view of the aerosol provision system in a coupled configuration.

As seen in FIG. 1B and the cut-away view illustrated in FIG. 1C, the aerosol provision device 141 and consumable 142 each include a number of respective components. The components illustrated in FIG. 1C are representative of the components that may be present in an aerosol provision device and consumable and are not intended to limit the scope of components that are encompassed by the present disclosure.

The aerosol provision device 141 may include a housing 145 (sometimes referred to as an aerosol provision device shell) that may include a power source 150. The housing may also include circuitry 152 with a switch in the form of a sensor 154, a user interface including a light source 156 that may be illuminated with use of the aerosol provision system 140, and processing circuitry 158 (also referred to as a control component). The housing may also include a receptacle in the form of a consumable receiving chamber 162 structured to engage and hold the consumable 142. And the consumable may include an aerosol-generating material 164 that may correspond to aerosol-generating material 124, and that may include one or more of each of a number of constituents such as an active substance, flavorant, aerosol-former material or other functional material.

As also seen in FIG. 1C, the aerosol provision device 141 may also include electrical connectors 166 positioned in the consumable receiving chamber 162 configured to electrically couple the circuitry and thereby the aerosol provision device with the consumable 142, and in particular electrical contacts 168 on the consumable. In this regard, the electrical connectors and electrical contacts may form a connection interface of the aerosol provision device and consumable. As also shown, the aerosol provision device may include an external electrical connector 170 to connect the aerosol provision device with one or more external devices. Examples of suitable external electrical connectors include USB connectors, proprietary connectors such as Apple's Lightning connector, and the like.

In various examples, the consumable 142 includes a tank portion and a mouthpiece portion. The tank portion and the mouthpiece portion may be integrated or permanently fixed together, or the tank portion may itself define the mouthpiece portion (or vice versa). In other examples, the tank portion and the mouthpiece portion may be separate and removably engaged with one another.

The consumable 142, tank portion and/or mouthpiece portion may be separately defined in relation to a longitudinal axis (L), a first transverse axis (T1) that is perpendicular to the longitudinal axis, and a second transverse axis (T2) that is perpendicular to the longitudinal axis and is perpendicular to the first transverse axis. The consumable can be formed of a housing 172 (sometimes referred to as the consumable shell) enclosing a reservoir 174 (in the tank portion) configured to retain the aerosol-generating material 164. In some examples, the consumable may include an aerosol generator, such as electric heater 144 in the illustrated example. In some examples, the electrical connectors 166 on the aerosol provision device 141 and electrical contacts 168 on the consumable may electrically connect the electric heater with the power source 150 and/or circuitry 152 of the aerosol provision device.

As shown, in some examples, the reservoir 174 may be in fluid communication with an aerosol-generating material transfer component 176 adapted to wick or otherwise transport aerosol-generating material 164 stored in the reservoir housing to the electric heater 144. At least a portion of the aerosol-generating material transfer component may be positioned proximate (e.g., directly adjacent, adjacent, in close proximity to, or in relatively close proximity to) the electric heater. The aerosol-generating material transfer component may extend between the electric heater and the aerosol-generating material stored in the reservoir, and at least a portion of the electric heater may be located above a proximal end the reservoir. For the purposes of the present disclosure, it should be understood that the term "above" in this particular context should be interpreted as meaning toward a proximal end of the reservoir and/or the consumable 142 in direction substantially along the longitudinal axis (L). Other arrangements of the aerosol-generating material transfer component are also contemplated within the scope of the disclosure. For example, in some example implementations, the aerosol-generating material transfer component may be positioned proximate a distal end of the reservoir and/or arranged transverse to the longitudinal axis (L).

The electric heater 144 and aerosol-generating material transfer component 176 may be configured as separate elements that are fluidly connected, the electric heater and aerosol-generating material transfer component or may be configured as a combined element. For example, in some implementations an electric heater may be integrated into an aerosol-generating material transfer component. Moreover, the electric heater and the aerosol-generating material transfer component may be formed of any construction as otherwise described herein. In some examples, a valve may be positioned between the reservoir 174 and electric heater, and configured to control an amount of aerosol-generating material 164 passed or delivered from the reservoir to the electric heater.

An opening 178 may be present in the housing 172 (e.g., at the mouth end of the mouthpiece portion) to allow for egress of formed aerosol from the consumable 142.

As indicated above, the circuitry 152 of the aerosol provision device 141 may include a number of electronic components, and in some examples may be formed of a circuit board such as a PCB that supports and electrically connects the electronic components. The sensor 154 (switch) may be one of these electronic components positioned on the circuit board. In some examples, the sensor may comprise its own circuit board or other base element to which it can be attached. In some examples, a flexible circuit board may be utilized. A flexible circuit board may be configured into a variety of shapes. In some examples, a flexible circuit board may be combined with, layered onto, or form part or all of a heater substrate.

In some examples, the reservoir 174 may be a container for storing the aerosol-generating material 164. In some examples, the reservoir may be or include a fibrous reservoir with a substrate with the aerosol-generating material present on or in a support. For example, the reservoir can comprise one or more layers of nonwoven fibers substantially formed into the shape of a tube encircling the interior of the housing 172, in this example. The aerosol-generating material may be retained in the reservoir. Liquid components, for example, may be absorptively retained by the reservoir. The reservoir may be in fluid connection with the aerosol-generating material transfer component 176. The aerosol-generating material transfer component may transport the aerosol-generating material stored in the reservoir via capillary action—or via a micro pump—to the electric heater 144. As such, the electric heater is in a heating arrangement with the aerosol-generating material transfer component.

In use, when a user draws on the aerosol provision system 140, airflow is detected by the sensor 154, and the electric heater 144 is activated to energize the aerosol-generating material 164 to generate an aerosol. Drawing upon the mouth end of the aerosol provision system causes ambient air to enter and pass through the aerosol provision system. In the consumable 142, the drawn air combines with the aerosol that is whisked, aspirated or otherwise drawn away from the electric heater and out the opening 178 in the mouth end of the aerosol provision system.

Figure 1D:
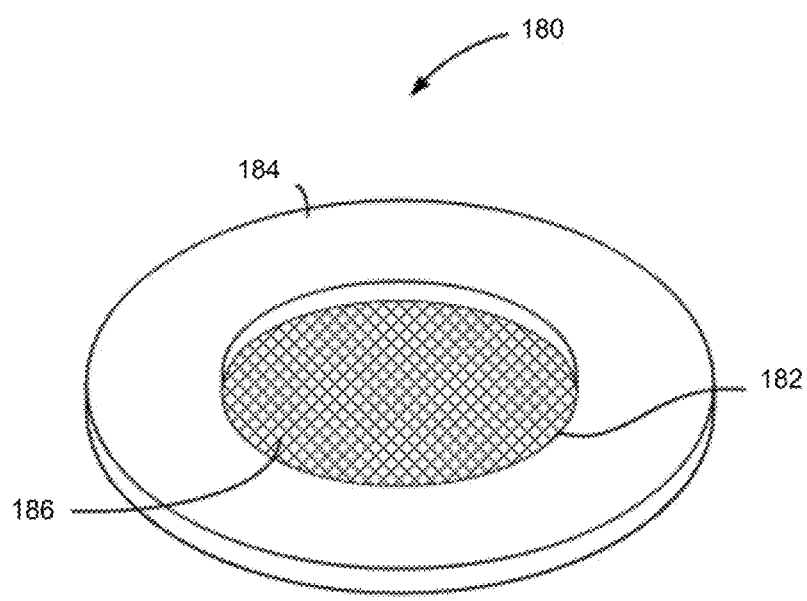
FIG. 1D illustrates a nebulizer that may be used to implement an aerosol generator of an aerosol provision system, according to some example implementations.

Again, as shown in FIGS. 1B and 1C, the aerosol generator of the aerosol provision system 140 is an electric heater 144 designed to heat the aerosol-generating material 164 to generate an aerosol. In other implementations, the aerosol generator is designed to break up the aerosol-generating material without heating, or with only secondary heating. FIG. 1D illustrates a nebulizer 180 that may be used to implement the aerosol generator of an aerosol provision system, according to some these other example implementations.

As shown in FIG. 1D, the nebulizer 180 includes a mesh plate 182 and a piezo material 184 that may be affixed to one another. The piezo material may be driven to vibrate and cause the mesh plate to break up aerosol-generating material into an aerosol. In some examples, the nebulizer may also include a supporting component located on a side of the mesh plate opposite the piezo material to increase the longevity of the mesh plate, and/or an auxiliary component between the mesh plate and the piezo material to facilitate interfacial contact between the mesh plate and the piezo material.

In various example implementations, the mesh plate 182 may have a variety of different configurations. The mesh plate may have a flat profile, a domed shape (concave or convex with respect to the aerosol-generating material), or a flat portion and a domed portion. The mesh plate defines a plurality of perforations 186 that may be substantially uniform or vary in size across a perforated portion of the mesh plate. The perforations may be circular openings or non-circular openings (e.g., oval, rectangular, triangular, regular polygon, irregular polygon). In three-dimensions, the perforations may have a fixed cross section such as in the case of cylindrical perforations with a fixed circular cross section, or a variable cross section such as in the case of truncated cone perforations with a variable circular cross section. In other implementations, the perforations may be tetragonal or pyramidal.

The piezo material 184 may be or include a piezoelectric material or a piezomagnetic material. A piezoelectric material may be coupled to circuitry configured to produce an oscillating electric signal to drive the piezoelectric material to vibrate. For a piezomagnetic material, the circuitry may produce a pair of antiphase, oscillating electric signals to drive a pair of magnets to produce antiphase, oscillating magnetic fields that drives the piezomagnetic material to vibrate.

The piezo material 184 may be affixed to the mesh plate 182, and vibration of the piezo material may in turn cause the mesh plate to vibrate. The mesh plate may be in contact with or immersed in aerosol-generating material, in sufficient proximity of aerosol-generating material, or may otherwise receive aerosol-generating material via an aerosol-generating material transfer component. The vibration of the mesh plate, then, may cause the aerosol-generating material to pass through the perforations 186 that break up the aerosol-generating material into an aerosol. More particularly, in some examples, aerosol-generating material may be driven through the perforations 186 in the vibrating mesh plate 182 resulting in aerosol particles. In other examples in which the mesh plate is in contact with or immersed in aerosol-generating material, the vibrating mesh plate may create ultrasonic waves within aerosol-generating material that cause formation of an aerosol at the surface of the aerosol-generating material.

As described above, hybrid products use a combination of aerosol-generating materials, and some hybrid products are similar to vapor products except that the aerosol generated from one aerosol-generating material may pass through a second aerosol-generating material to pick up additional constituents. Another similar aerosol provision system in the form of a hybrid product may therefore be constructed similar to the vapor product in FIGS. 1B and 1C (with an electric heater 144 or a nebulizer 180). The hybrid product may include a second aerosol-generating material through which aerosol from the aerosol-generating material 164 is passed to pick up additional constituents before passing through the opening 178 in the mouth end of the aerosol provision system.

Figure 2A:
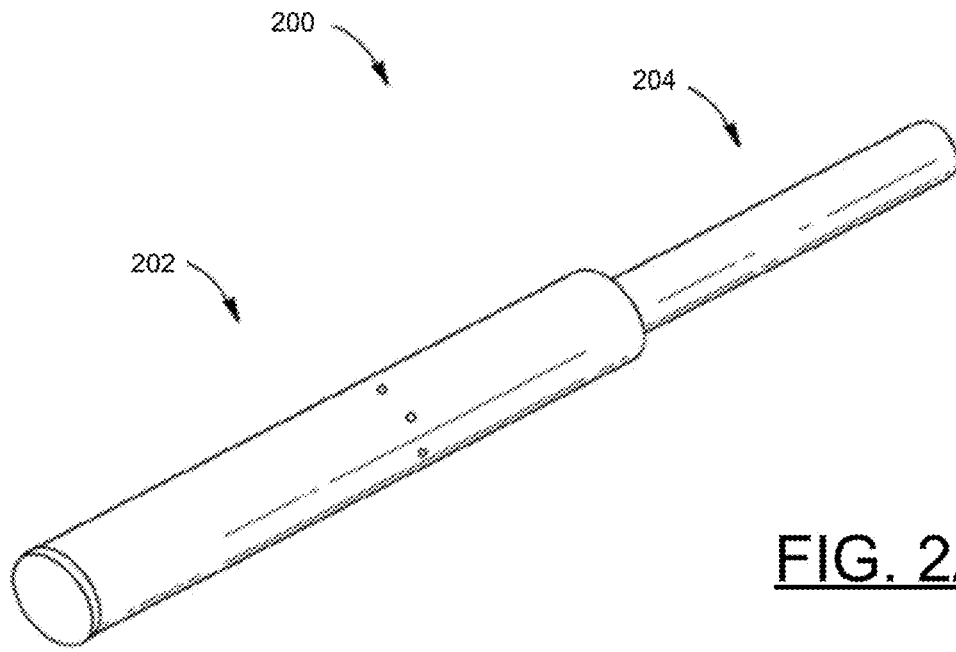
FIGS. 2A, 2B and 2C illustrate an aerosol provision system in the form of a heat-not-burn product, according to some example implementations.
Figure 2B:
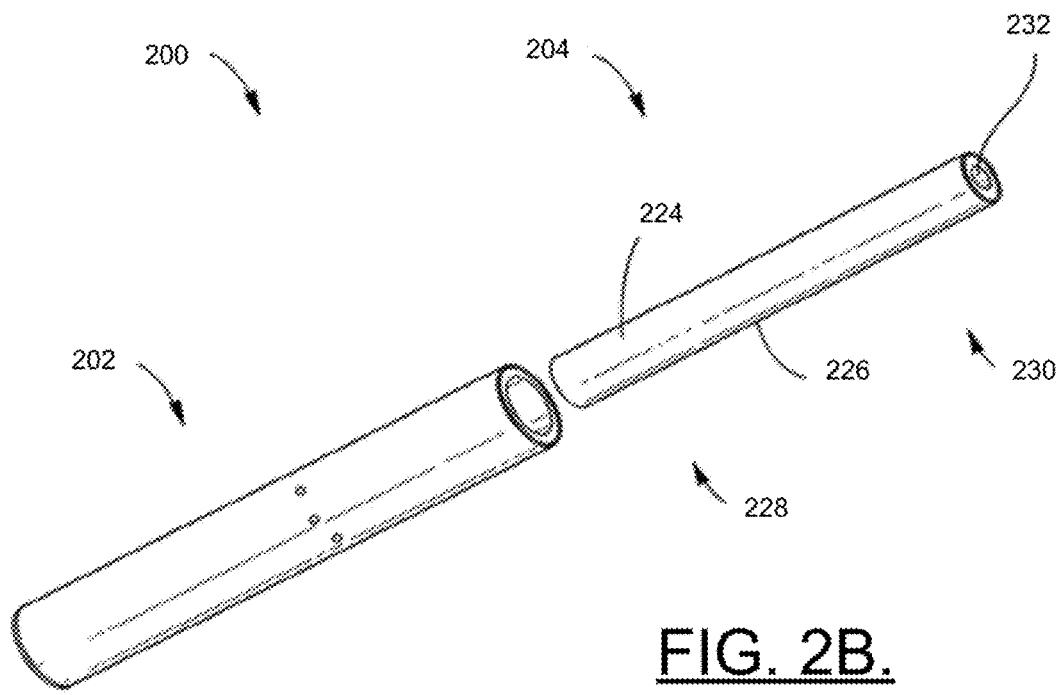
Figure 2C:
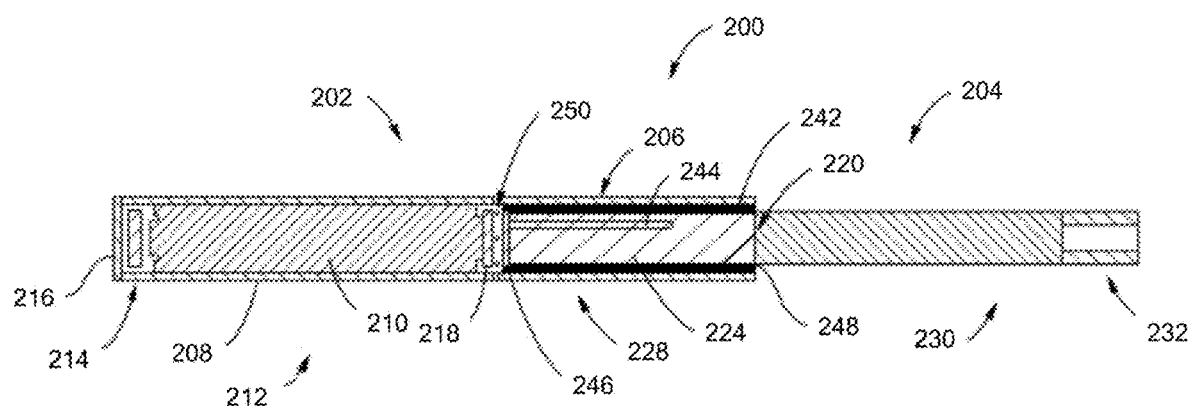

FIGS. 2A, 2B and 2C illustrate an aerosol provision system 200 in the form of a heat-not-burn product, and that in some example implementations may correspond to the aerosol provision system 100. As shown, the aerosol provision system may include an aerosol provision device 202 (also referred to as a control body or power unit) and a consumable 204 (also referred to as an aerosol source member or cartridge), which may correspond to respectively the aerosol provision device 102 and the consumable 104. The aerosol provision system and in particular the aerosol provision device may also include an aerosol generator corresponding to the aerosol generator 106, and in the form of an electric heater 206. The aerosol provision device and the consumable can be permanently or detachably aligned in a functioning relationship. FIG. 2A illustrates the aerosol provision system in a coupled configuration, whereas FIG. 2B illustrates the aerosol provision system in a decoupled configuration. FIG. 2C illustrates a partially cut-away side view of the aerosol provision system in the coupled configuration.

As seen in FIGS. 2A, 2B and 2C, the aerosol provision device 202 and consumable 204 each include a number of respective components. The components illustrated in the figures are representative of the components that may be present in an aerosol provision device and consumable and are not intended to limit the scope of components that are encompassed by the present disclosure.

The aerosol provision device 202 may include a housing 208 (sometimes referred to as an aerosol provision device shell) that may include a power source 210. The housing may also include circuitry 212 with a switch in the form of a sensor 214, a user interface including a light source 216 that may be illuminated with use of the aerosol provision system 200, and processing circuitry 218 (also referred to as a control component). In some examples, at least some of the electronic components of the circuitry may be formed of a circuit board or a flexible circuit board that supports and electrically connects the electronic components.

The housing 208 may also include a receptacle in the form of a consumable receiving chamber 220 structured to engage and hold the consumable 204. The consumable 204 may include an aerosol-generating material 224 that may correspond to aerosol-generating material 124, and that may include one or more of each of a number of constituents such as an active substance, flavorant, aerosol-former material or other functional material. And the aerosol-generating material may be present on or in a support to form a substrate 226.

In the coupled configuration of the aerosol provision system 200, the consumable 204 may be held in the receiving chamber 220 in varying degrees. In some examples, less than half or approximately half of the consumable may be held in the receiving chamber 220. In other examples, more than half of the consumable 204 may be held in the receiving chamber 220. In yet other examples, substantially the entire consumable 204 may be held in the receiving chamber 220.

As shown in FIGS. 2B and 2C, in various implementations of the present disclosure, the consumable 204 may include a heated end 228 sized and shaped for insertion into the aerosol provision device 202, and a mouth end 230 upon which a user draws to create the aerosol. In various implementations, at least a portion of the heated end may include the aerosol-generating material 224.

In some example implementations, the mouth end 230 of the consumable 204 may include a filter 232 made of a material such as cellulose acetate or polypropylene. The filter may additionally or alternatively contain strands of tobacco containing material. In some examples, at least a portion of the consumable may be wrapped in an exterior overwrap material, which may be formed of any material useful to provide additional structure, support and/or thermal resistance. In some examples, an excess length of the overwrap at the mouth end of the consumable may function to simply separate the aerosol-generating material 224 from the mouth of a user or to provide space for positioning of a filter material, or to affect draw on the consumable or to affect flow characteristics of the aerosol leaving the consumable during draw.

The electric heater 206 may perform electric heating of the aerosol-generating material 224 by resistance (Joule) heating, induction heating, dielectric and microwave heating, radiant heating, arc heating and the like. The electric heater may have a variety of different configurations. In some examples, at least a portion of the electric heater may surround or at least partially surround at least a portion of the consumable 204 including the aerosol-generating material when inserted in the aerosol provision device 202. In other examples, at least a portion of the electric heater may penetrate the consumable when the consumable is inserted into the aerosol provision device. In some examples, the substrate 226 material may include a susceptor, which may be embedded within the aerosol-generating material, or on one or either side of the aerosol-generating material.

Although shown as a part of the aerosol provision device 202, the electric heater 206 may instead be a part of the consumable 504. In some examples, the electric heater or a part of the electric heater may be may be combined, packaged or integral with (e.g., embedded within) the aerosol-generating material 224.

As shown, in some examples, the electric heater 206 may extend proximate an engagement end of the housing 208, and may be configured to substantially surround a portion of the heated end 228 of the consumable 204 that includes the aerosol-generating material 224. The electric heater 206 may be or may include an outer cylinder 242, and one or more resistive heating elements 244 such as prongs surrounded by the outer cylinder to create the receiving chamber 220, which may extend from a receiving base 246 of the aerosol provision device to an opening 248 of the housing 208 of the aerosol provision device. In some examples, the outer cylinder may be a double-walled vacuum tube constructed of stainless steel so as to maintain heat generated by the resistive heating element(s) within the outer cylinder, and more particularly, maintain heat generated by the resistive heating element(s) within the aerosol-generating material.

Like the electric heater 206, the resistive heating element(s) 244 may have a variety of different configurations, and vary in number from one resistive heating element to a plurality of resistive heating elements. As shown, the resistive heating element(s) may extend from a receiving base 246 of the aerosol provision device 202. In some examples, the resistive heating element(s) may be located at or around an approximate radial center of the heated end 228 of the consumable 204 when inserted into the aerosol provision device. In some examples, the resistive heating element(s) may penetrate into the heated end of the consumable and in direct contact with the aerosol-generating material. In other examples, the resistive heating element(s) may be located inside (but out of direct contact with) a cavity defined by an inner surface of the heated end of the consumable.

In some examples, the resistive heating element(s) 244 of the electric heater 206 may be connected in an electrical circuit that includes the power source 210 such that electric current produced by the power source may pass through the resistive heating element(s). The passage of the electric current through the resistive heating element(s) may in turn cause the resistive heating element(s) to produce heat through resistance (Joule) heating.

In other examples, the electric heater 206 including the outer cylinder 242 and the resistive heating element(s) 244 may be configured to perform induction heating in which the outer cylinder may be connected in an electrical circuit that includes the power source 210, and the resistive heating element(s) may be connected in another electrical circuit. In this configuration, the outer cylinder and resistive heating element(s) may function as a transformer in which the outer cylinder is an induction transmitter, and the resistive heating element(s) is/are an induction receiver. In some of these examples, the outer cylinder and the resistive heating element(s) may be parts of the aerosol provision device 202. In other of these examples, the outer cylinder may be a part of the aerosol provision device, and the resistive heating element(s) may be a part of the consumable 204.

The outer cylinder 242 may be provided with an alternating current directly from the power source 210, or indirectly from the power source in which an inverter (as part of the circuitry 212) is configured to convert direct current from the power source to an alternating current. The alternating current drives the outer cylinder to generate an oscillating magnetic field, which induces eddy currents in the resistive heating element(s) 244. The eddy currents in turn cause the resistive heating element(s) to generate heat through resistance (Joule) heating. In these examples, the resistive heating element(s) may be wirelessly heated to form an aerosol from the aerosol-generating material 224 positioned in proximity to the resistive heating element(s).

In various example implementations, the aerosol provision device 202 may include an air intake 250 (e.g., one or more openings or apertures) in the housing 208 (and perhaps also the receiving base 246) to enable airflow into the receiving chamber 220. When a user draws on the mouth end 228 of the consumable 204, the airflow may be drawn through the air intake into the receiving chamber, pass into the consumable, and be drawn through the aerosol-generating material 224. The airflow may be detected by the sensor 214, and the electric heater 206 may be activated to energize the aerosol-generating material to generate an aerosol. The airflow may combine with the aerosol that is whisked, aspirated or otherwise drawn out an opening at the mouth end of the aerosol provision system. In examples including the filter 232, the airflow combined with the aerosol may be drawn out an opening of the filter at the mouth end.

Figure 3:
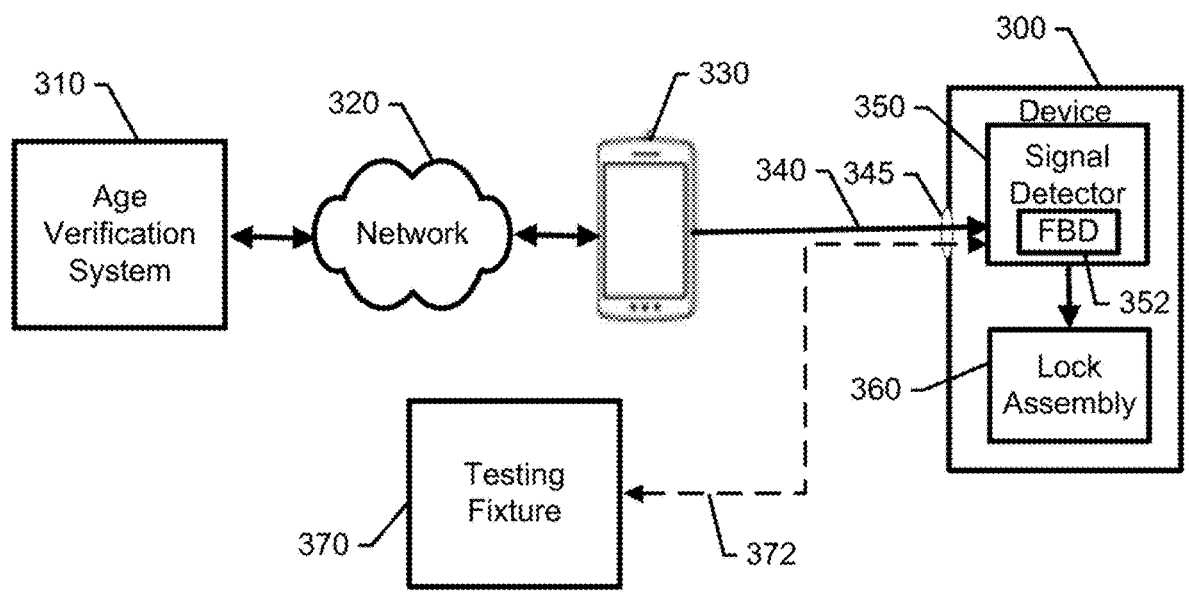
FIG. 3 is a block diagram of an example implementation of devices associated with a PSA process in accordance with an example embodiment.

As noted above, PSA may be desirable after purchase or acquisition of the aerosol provision devices 102/202 of FIGS. 1 and 2, or other devices like them. FIG. 3 illustrates an example system diagram for functional control of a device 300 (which may be an example of the aerosol provision devices 102/202 of FIGS. 1 and 2) for PSA in accordance with an example embodiment. In this regard, FIG. 3 illustrates how the device 300 communicates with an age verification system 310 through a network 320 and a host device 330, in order to verify the user's age, which may also be used to authenticate the device 300 periodically. The device 300 may be in a locked state (e.g., in which the device 300 is unusable or such usage is strictly controlled) until authenticated properly via the PSA process. After authentication, the device 300 may be unlocked and operate normally. The age verification system 310 may be operably coupled with the host device 330 over the network 320. Although not shown, the age verification system 310 may be coupled with the device 300 over the network 320.

The device 300 may be any aerosol delivery device, including for example an electronic nicotine delivery systems ("ENDS") device according to various embodiments described above. In one embodiment, the age verification system 310 may not only verify an age (e.g. for an age restricted product), but may also provide authentication or user identification (e.g. for an actual purchase or to prevent theft). An example of the authentication and age verification by the age verification system 310 is further described in U.S. patent application Ser. No. 16/415,460, entitled "AUTHENTICATION AND AGE VERIFICATION FOR AN AEROSOL DELIVERY DEVICE," which claims priority to U.S. Provisional App. No. 62/282,222 on Apr. 2, 2019, the entire disclosures of each of which are hereby incorporated by reference. The authentication described below may rely on age verification being performed first and then referenced for subsequent authentication using a control signal 340 sent to the device 300. However, there may be other verification mechanisms other than age. For example, in some embodiments, user identification may be performed in lieu of age verification. Thus, for example, the age verification system 310 is more generally simply an example of an authorization system that is configured to conduct PSA for the device 300, and the age verification system 310 may therefore more generally be referred to as an authentication agent. Cartridges or consumables may be registered as part of the age verification or authentication process as described in U.S. patent application Ser. No. 16/415,444, entitled "AGE VERIFICATION WITH REGISTERED CARTRIDGES FOR AN AEROSOL DELIVERY DEVICE," filed on May 17, 2019, the entire disclosure of which is herein incorporated by reference. U.S. Pat. No. 8,689,804 to Fernando et al. discloses identification systems for smoking devices, the disclosure of which is being incorporated herein by reference.

The age verification system 310 may include a database that tracks users along with ages, as well as maintains a record of the devices and components (e.g. cartridges) along with approvals. It may be encrypted and/or use anonymous identifiers (e.g. numbers, letters, or any alphanumeric identifiers) for each user.

The initial age verification may occur and be stored in the database, such as may be maintained at the age verification system 310 and/or otherwise accessible over the network 320. In some embodiments, age verification records may be maintained using blockchain technology. Future age verification requests by that user may be confirmed by calling the database. Specifically, once a user is initially age verified as confirmed in the age verification system database, future verifications (i.e. "authentications") may be merely calls to this database for unlocking the device 300. In other words, a user initially performs an age verification and then subsequent usage may require authentication without the complete initial age verification requirements. The frequency with which the device 300 must be unlocked or authenticated can vary. Likewise, the timing for when a user needs to re-verify their age (or otherwise re-authenticate themselves) may vary. For example, each time the cartridge is replaced, the user may need to re-verify or re-authenticate. In some embodiments, the re-authentication may be required after a certain number of puffs from the device 300 or may be based on the passage of time (e.g. once per hour, day, week, month, etc.). The online database may track the requests for authentication and set limits per user. This can prevent the potential fraud of a single user unlocking other under-age user's devices. This also would prevent the re-distribution of unlocked (i.e. verified and authenticated) devices and/or accessories. Reasonable limits for the number of devices, chargers, consumables, and/or authentications can prevent this potential fraud.

A user profile may be stored (e.g. on the device 300 or from an application or app on a host device 330) that includes an age verified identity for the user. An app on the host device 330 may access the user profile over a network, such as the network 320. Once a user is initially age verified as confirmed in the age verification system database, the user profile for that user may be generated and saved so that future verifications (i.e. "authentications") may be merely calls to this database. In one embodiment, the age verification may be a prerequisite for the host device 330 to be able to generate and submit the control signal 340 to the device 300.

The host device 330 may be any computing or communication device, such as a smartphone, tablet, cellular phone, analog phone, computer, or dedicated authentication device at a point of sale. The host device 330 may communicate with or provide the control signal 340 to the device 300 for authentication or activation. The control signal 340 from the host device 320 to the device 300 may be a wired or a wireless signal such as, for example an RF signal, a vibratory signal, an audio signal or a light/optical signal. Optical signals should be understood to include those in the visible light spectrum, but also infra-red signals, fiber optic signals, ultraviolet light signals as well as signals associated with intensity tuning or wavelength tuning. Audible signals should be understood to include those in and outside the audible range for humans. Moreover, audible signals that employ decibel tuning or frequency tuning may also be included. In some embodiments, the host device 330 may therefore couple audibly or optically with the device 300 in order to communicate the control signal 340 to authenticate and/or unlock the device 300. Thus, the ability of the host device 330 with respect to transmission of the control signal 340, and the environmental factors that may impact receipt of the control signal 340 at the device 300 are all important to successful authentication or authorization of the device 300.

Particularly for examples in which the control signal 340 is an optical signal or audio signal, the device 300 may include an aperture 345 formed in a housing of the device 300. The aperture 345 may in turn provide access for the audio or optical signal that is an example of the control signal 340 to reach a signal detector 350. The signal detector 350 may interface with a lock assembly 360 to alternately lock or unlock the device 300 as described herein. In some cases, the signal detector 350 may further include a feedback device (FBD) 352 that is configured to provide visual, haptic and/or audible feedback to the user relating to the success or failure of attempts to unlock the device 300 (or other status information). In some cases, the feedback device 352 may include, vibrating components, lights (e.g., one or more light emitting diodes (LEDs)) or speakers that provide an output responsive to successful or failed efforts to operate the lock assembly 360. In an example embodiment, a different color or sequence of lights, or a different sound or tonal pattern may indicate success and failure or even other status information.

In an example embodiment, the signal detector 350 may be configured to process the control signal 340 to utilize or extract an unlock code therein for PSA. Thus, in a context in which the control signal 340 is an optical signal, audio signal, an RF signal or a vibratory signal, it should be appreciated that the signal detector 350 is configured to process the control signal 340 to determine the unlock code for provision to the lock assembly 360 to unlock the lock assembly 360 using the unlock code.

The lock assembly 360 may be configured to prevent operation of the device 300 for generating an aerosol when the device 300 is in a locked state, and enable operation of the device 300 for generating the aerosol when the device 300 is in an unlocked state. For example, when in the locked state, the lock assembly configured to prevent operation of the aerosol generator 106 of FIG. 1 with respect to generating the aerosol, and enable operation of the aerosol generator 106 for generating the aerosol in the unlocked state. The lock assembly 360 may be the last step in the PSA process (or one of the last steps), and may apply the unlock code (or unique code) provided in the control signal 340 to transition from the locked state to the unlocked state if the unlock code is authenticated. As such, the signal detector 350 may receive the control signal 340 and process the control signal 340 using appropriate techniques to obtain the unlock code from the control signal 340 and provide the unlock code to the lock assembly 360. If authenticated, the lock assembly 360 may enable the device 300 to be shifted to the unlocked state to enable aerosol generation, thereby successfully completing the PSA process.

As noted above, the control signal 340 may be a wireless signal that may be, for example, optical or audible. General information regarding processing the control signal 340 as an optical signal is provided in U.S. patent application Ser. No. 16/441,937, entitled "FUNCTIONAL CONTROL AND AGE VERIFICATION OF ELECTRONIC DEVICES THROUGH VISUAL COMMUNICATION," filed on Jun. 14, 2019, the entire disclosure of which is herein incorporated by reference. Similarly, information regarding processing the control signal 340 as an audible signal is provided in U.S. patent application Ser. No. 16/441,903, entitled "FUNCTIONAL CONTROL AND AGE VERIFICATION OF ELECTRONIC DEVICES THROUGH SPEAKER COMMUNICATION," filed on Jun. 14, 2019, the entire disclosure of which is herein incorporated by reference. The signal detector 350 may be configured to provide processing for the control signal 340 in either context.

To the extent a user obtains the device 300 and attempts to perform PSA in the manner generally described above, but the attempted PSA fails due to limitations of the host device 330 or various technical or environmental factors, the user may become irritated or annoyed. Meanwhile, if the PSA attempt proceeds smoothly for the user, the likelihood of user satisfaction, positive reviews, and continued sales of such devices may be increased. Thus, to provide a higher likelihood of a positive user experience associated with PSA, example embodiments may provide the ability to ensure that the device 300 is fully equipped to operate as intended to perform PSA by ensuring that each of the signal detector 350 and the lock assembly 360 are functionally tested to operate properly as described in greater detail below.

In an example embodiment, a testing fixture 370 may be operably coupled to the device 300 to test the device 300 functionally before the device 300 is sold or distributed in order to provide this ability. In this regard, for example, the testing fixture 370 may be configured to interface with the signal detector 350 to provide test signaling 372. The test signaling 372 may pass through the aperture 345 formed in a housing of the device 300, and otherwise cause the signal detector 350 to operate as described above to operate the lock assembly 360 to transition to the unlocked state, and then transition back into the locked state. As such, the testing fixture 370 may be configured to cycle the device 300 through the unlocked and locked states to confirm that the device 300 operates properly for PSA. The testing fixture 370 may also confirm other information about the device 300 (e.g., a unique identifier or unique ID of the device 300) in preparation for enabling the device 300 to be sold or otherwise distributed and then unlocked by the user who purchases the device 300. Operation of the testing fixture 370 and various structures, devices or components that may be employed in the testing fixture 370 will now be described in reference to FIGS. 4-7.

FIG. 4 illustrates a schematic diagram of one example implementation of the testing fixture 370. In this regard, FIG. 4 illustrates externally visible features or structures of the testing fixture 370, and other figures will show internal features or components. In this example, the testing fixture 370 may have a housing 400 that houses or otherwise includes a plurality of testing modules 410. The housing 400 may be a rigid structure supporting each of the testing modules 410 and, in some cases, the testing modules 410 themselves may be removable and/or replaceable to either repair or replace a damaged module, or replace modules configured to interface with one type of the device 300 with modules that are configured to interface with other and different types of the device 300.

Each of the testing modules 410 (e.g., testing modules #1, #2, #3, #4, . . . #N) may have a same or similar structure to other testing modules 410 used at any given time. Moreover, the testing modules 410 may be operated (or at least operable) simultaneously to conduct testing of multiple respective instances of the device 300 of FIG. 3. Thus, for example, an operator of the testing fixture 370 may insert an instance of the device 300 into each one of the testing modules 410. The testing modules 410 may then execute a testing procedure to test each instance of the device 300 for proper unlocking and locking operation. In some cases, the testing modules 410 may also be used to extract or confirm other information from each instance of the device 300 as well. For example, in some embodiments, the testing modules 410 may read the unique ID of each instance of the device 300. Moreover, in some examples, the unlocking operation may be conducted using an unlock code that is generated based on (and in some cases specific to) the unique ID. Thus, for example, the test modules 410 may learn or extract the unique ID for the device 300 in a given one of the testing modules 410 (i.e., in its cavity 412) and reference a listing of corresponding unique unlock codes in a table (stored in memory 504 of FIG. 5). The unique unlock code for the corresponding unique ID used to enter the table may then be used to generate the unlock instruction for the device 300. As an alternative, the unique ID could form a basis for generating the unique unlock code. In either example case, the memory 504 may store instructions for generation of the unique unlock code based on the unique ID provided.

Figure 4:
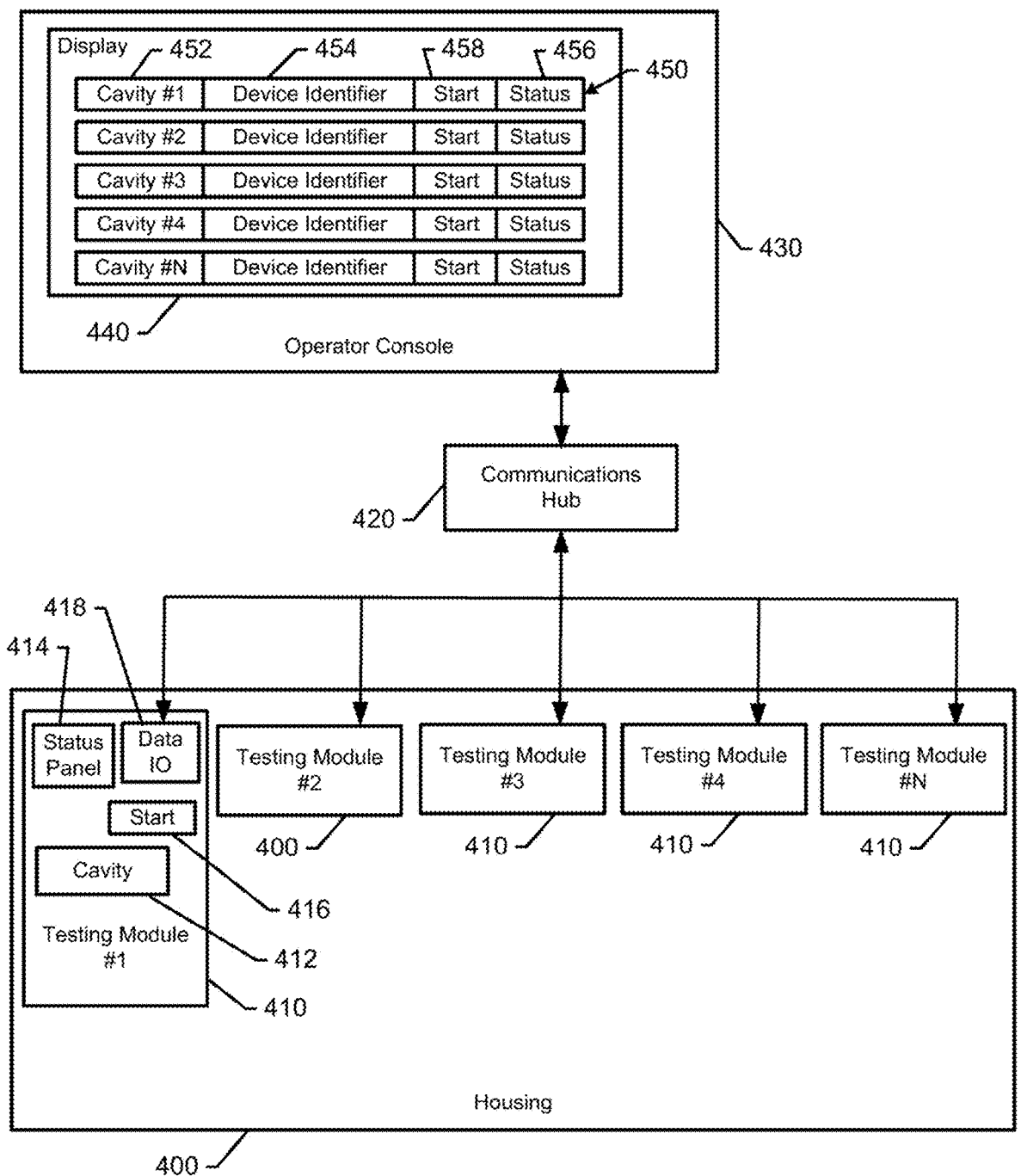
FIG. 4 is a schematic diagram of a test fixture in accordance with an example embodiment.

In an example embodiment, each of the testing modules 410 may include the additional components or structures shown in FIG. 4 in association with testing module #1. In this regard, each of the testing modules 410 may include a cavity 412 into which a portion of the device 300 (e.g., the housing 208 of the aerosol provision device 202 or the housing 145 of the aerosol provision device 141 described above) may be inserted. In other words, the non-consumable or power unit portion of the device 300 may be inserted into the cavity 412. As such, the cavity 412 may be defined as an elongated slot that is shaped and formed to receive the power unit of the device 300. Thus, the cavity 412 may have a cylindrical shape, a rectangular prism shape, or various perturbations of these or other shapes in order to receive and support the power unit of the device 300 that the testing fixture 370 is designed to test. In many cases, the cavity 412 may be provided at the front side or front panel of the housing 400. In such cases, the cavity 412 will typically extend into the housing 400 in a direction parallel to the surface on which the housing 400 is supported. However, the cavities 412 may alternatively be on a sidewall of the housing 400 or another accessible surface or wall of the housing 400 such as the top surface. When provided at the top surface of the housing 400, the cavity 412 may extend in a downward direction normal or perpendicular to the surface on which the housing 400 is supported. Thus, one of skill in the art will easily appreciate that in one instance FIG. 4 illustrates a front face (or side face) of the housing 400 so that the surface is at the bottom of the housing 400 as the housing 400 appears on the page. Meanwhile, in another alternative, FIG. 4 could be appreciated to show a top face of the housing 400 such that the surface is behind the housing 400 as the housing 400 appears on the page.

Each of the testing modules 410 may also include a status panel 414 to show a status of testing conducted on the power unit of the device 300 in the corresponding one of the testing modules 410 and a start button 416 (or a key, switch, lever, or other operable member) used as a user interface element for starting (or pausing) a test for the device in the corresponding one of the testing modules 410. The operator may therefore insert the power unit of the device 300 into a selected one of the testing modules 410 (e.g., testing module #1) and press the start button 416 of the selected one of the testing modules 410 to begin a test on the power unit of the device 300. While that test begins or is in progress, the operator may insert the power unit of another instance of the device 300 into an adjacent (or any other) one of the testing modules 410 (e.g., testing module #2) and press the start button 416 of the adjacent (or other) one of the testing modules to begin a test on the power unit of the other instance of the device 300. This process may be repeated for each of the testing modules 410 until, for example, all testing modules 410 have an instance of the device 300 therein and are conducting or have completed conducting a test on the instance of the device 300. The operator can continue to cycle through inserting, testing, withdrawing and inserting new devices in each of the cavities until a full batch of devices has been tested.

Each of the testing modules 410 may also include a data input/output (TO) port 418. In some cases, the data input/output port 418 may be a universal serial bus (USB) port or other standard interface port. However, proprietary connections may alternatively be employed in some examples. Notably, although FIG. 4 shows five testing modules 410, example embodiments are scalable to include any desirable number of the testing modules 410. In this regard, for example, the average time it takes to conduct a test may be balanced against the number of cavities so that a relatively continuous process of cycling through insertion of devices, initiation of testing, and replacement of the inserted devices with devices needing to be tested after testing of already inserted devices is complete may efficiently be performed.

Each of the data input/output ports 418 of the testing modules 410 may be operably coupled to a common point or device such as a communications hub 420. The communications hub 420 of this example may be a USB bank configured to connect each of the testing modules 410 to an operator console 430 for output of information associated with the testing processes being conducted at each respective one of the testing modules 410. Thus, for example, if five testing modules are included (i.e., N=5) as shown in the example of FIG. 4, the communications hub 420 may receive information from each of the testing modules 410 for provision to the operator console 430 via one data line (e.g., a single cable or connection), which may be wired or wireless.

The operator console 430 may include a display 440 and any of a number of user interface components (e.g., a keyboard, mouse, touch screen interface, etc.). The operator console 430 may therefore, in some cases, be a standalone computer or laptop. However, in other cases, the operator console 430 may be collection of individual user interface components such as the display 440 and a mouse, keyboard, etc. As such, it should be appreciated that the housing 400 may be connected to different operator consoles, or different components that may act as the operator console 430, and example embodiments and testing methods may still be practiced. In other words, the testing fixture 370 of example embodiments may be interchangeably connected to a number of different output devices or operator consoles. Thus, for example, an operator may obtain one or more instances of the testing fixture 370 and operably couple the instances of the testing fixture 370 with any suitable components or devices that can act as the operator console 430 and no special equipment may be needed to act as the operator console 430.

However, in other instances, the testing fixture 370 may be configured to stand entirely alone, and operate testing described herein without any external connections. In such examples, either the communications hub 420 and the operator console 430 may be internalized or parts of the testing fixture 370, or the testing fixture 370 may independently operate using just the start button 416 to start testing and the status panel 414 to indicate whether the test has passed or failed (or is in progress). For example, the status panel 414 may include a green light indicating a pass and a red light indicating a fail. Other lights, or simply patterns of flashing for the lights, may be used to indicate other statuses (e.g., testing in progress, time remaining for a test, test phase in progress, etc.).

In such an example, the data associated with testing for each power unit of the device 300 may be recorded in association with the unique ID of the corresponding device. Thus, for example, the start button 416 may be part of a keyboard or data entry panel via which the unique ID of each instance of the device 300 may be entered. Alternatively, the testing modules 410 may be configured to automatically read and determine the unique ID directly from the device 300. In either case, testing data may be recorded in association with each unique ID and stored locally at the testing fixture 370. The data input/output port 418 may then be used at a later time to transfer data associated with each of the unique IDs tested to an external device (e.g., the operator console 430). The data may then be displayed at the external device or otherwise be analyzed to determine patterns or clues that may be used to improve the testing process, or the locking/unlocking operations that are generally conducted for the device 300 as described above. Alternatively, the data may be displayed on the display 440 either in real time or post hoc for analysis or use by the operator.

As shown in FIG. 4, the display 440 may provide device information 450 for each respective instance of the device 300 in respective cavities 412 of the testing modules 410. The device information 450 may include a cavity identifier 452, a device identifier 454 that provides the unique ID for the respective instance of the device 300, and status information 456 associated with the testing. Although not required, in some cases, the device information 450 may also include a soft key such as a start button 458, which may be used to control initiation, pausing, or other control over the conduct of testing at the operator console 430 instead of locally at the housing 400 (and at each individual one of the testing modules 410 using the start button 416).

Figure 5:
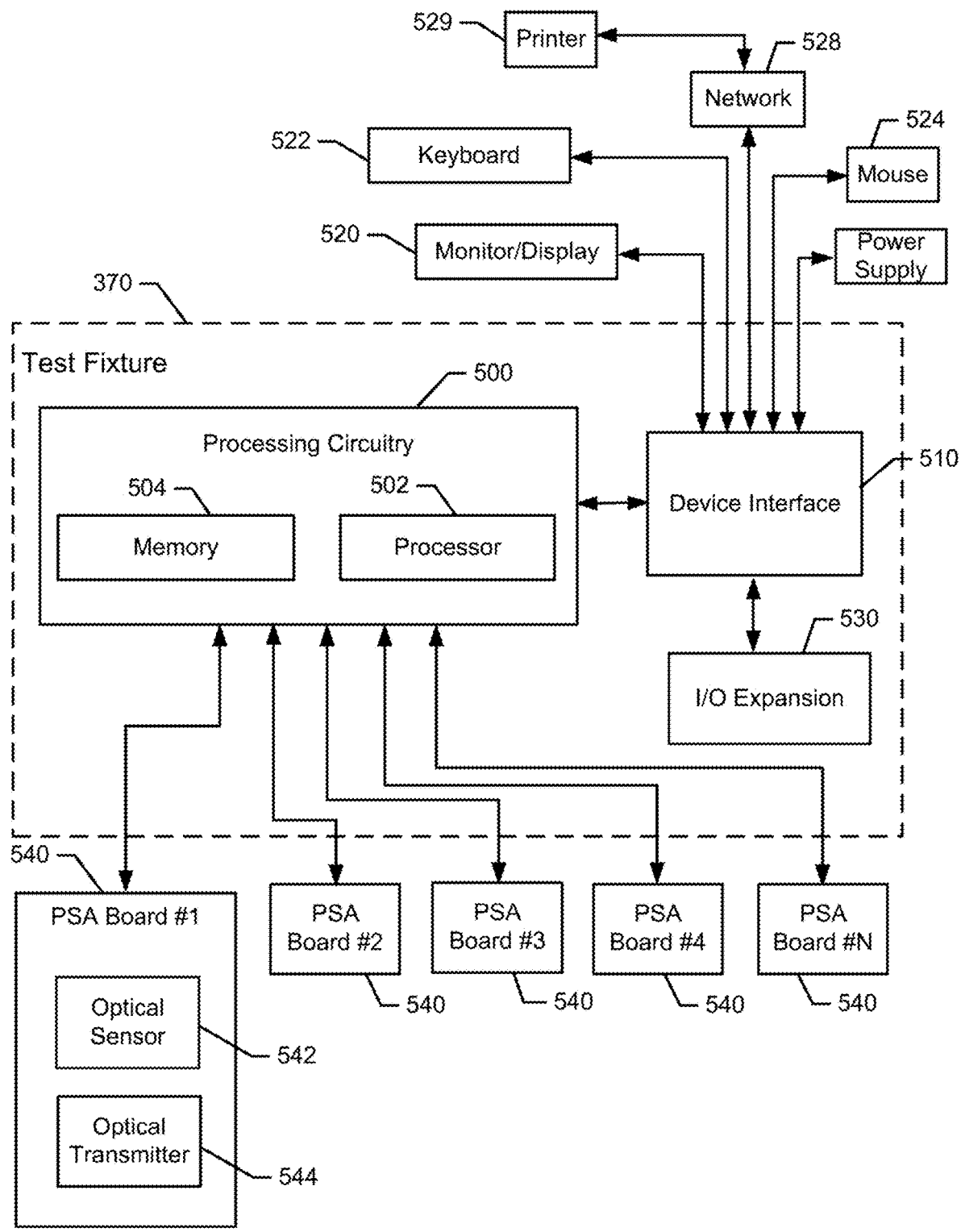
FIG. 5 is a functional block diagram of a test fixture in accordance with an example embodiment.

FIG. 5 illustrates a functional block diagram of various components of the test fixture 370 of an example embodiment. The test fixture 370 may include processing circuitry 500 configured to perform data processing, control function execution and/or other processing and management services according to an example embodiment. In some embodiments, the processing circuitry 500 may be embodied as a chip or chip set. In other words, the processing circuitry 500 may comprise one or more physical packages (e.g., chips) including materials, components and/or wires on a structural assembly (e.g., a baseboard). The structural assembly may provide physical strength, conservation of size, and/or limitation of electrical interaction for component circuitry included thereon. The processing circuitry 500 may therefore, in some cases, be configured to implement an embodiment of the present invention on a single chip or as a single "system on a chip." As such, in some cases, a chip or chipset may constitute means for performing one or more operations for providing the functionalities described herein.

In an example embodiment, the processing circuitry 500 may include one or more instances of a processor 502 and memory 504 that may be in communication with or otherwise control a device interface 510. As such, the processing circuitry 500 may be embodied as a circuit chip (e.g., an integrated circuit chip) configured (e.g., with hardware, software or a combination of hardware and software) to perform operations described herein. However, in some embodiments, the processing circuitry 500 may be embodied as a portion of an on-board computer.

The device interface 510 may include one or more interface mechanisms for enabling communication with other devices (e.g., modules, entities, and/or other components of the test fixture 370, of the control console 430 of FIG. 4, or the like). In some cases, the device interface 510 may be any means such as a device or circuitry embodied in either hardware, or a combination of hardware and software that is configured to receive and/or transmit data from/to modules, entities, and/or other components that are in communication with the processing circuitry 500 (directly or indirectly).

The device interface 510 may, in some cases, connect the processing circuitry 500 to internal and/or external components that combine to form a user interface for the test fixture 370. In FIG. 5, those user interface components are shown to include a monitor/display 520 (which may be the display 440 of FIG. 4, or one or all of the status panels 414 associated with each of the testing modules 410), a keyboard 522, and a mouse 524. The mouse 524 and keyboard 522 may be parts of the operator console 430 of FIG. 4 or separate components. If separate, the mouse 524 and keyboard 522 may be operably coupled to the processing circuitry 500 via standard connections (e.g., USB) or via proprietary means. Similarly, the monitor/display 520 may have any of a number of connection means including, for example, HDMI. Moreover, the device interface 510 may also or alternatively be operably coupled to other components that provide an audible, visual, mechanical or other output to the user such as, for example, speakers, switches, indicator lights, buttons or keys (e.g., function buttons), and/or other input/output mechanisms.

In some embodiments, the device interface 510 may also operably couple the test fixture 370 to a power supply 526. Thus, for example, the device interface 510 may include power control circuitry for converting AC to DC power (or vice versa) to power the electrical components of the test fixture 370. Thus, the power supply 526 could be mains power or battery power, regardless of the individual power needs of the components of the test fixture 370.

In some embodiments, the device interface 510 may also operably coupled the test fixture 370 to external components for analysis, remote monitoring, or other purposes via a network 528 that may be operably coupled to the processing circuitry 500 via Ethernet or other networking technologies. The network 528 may be a local, private, public, or other communication network including, for example, a local area network (LAN) or the Internet. In some cases, the test fixture 370 may include an input/output (I/O) expansion port 530. The input/output expansion port 530 may enable any of a number of additional devices, components, or modules to be operably coupled to the test fixture 370. Thus, for example, the input/output port 530 could be used to connect the test fixture 370 directly to external devices (i.e., without a network connection) or may be used to expand the capacity of the test fixture 370 by enabling scaling of the number of testing modules 410 to which the test fixture 370 can be coupled. In some cases, the input/output expansion port 530 may be operably coupled to a printer 529, which may be used to print the unique ID of each individual one of the devices. However, the printer 529 could alternatively be located in or accessed via the network 528. As noted above, the unique ID may be used to generate the proper unique unlock code for each respective different instance of the device 300. Thus, the consumer or end user will need the unique ID in order to generate (e.g., via the host device 330) the correct unique unlock code to operate the lock assembly 360. By providing a printed label or other printed version of the unique ID, the information can be provided to the consumer or end user with the product after confirmation (by the test fixture 370) that the unique unlock code corresponding to the unique ID does indeed work to unlock the lock assembly 360.

The processor 502 may be embodied in a number of different ways. For example, the processor 502 may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. In an example embodiment, the processor 502 may be configured to execute instructions stored in the memory 504 or otherwise accessible to the processor 502. As such, whether configured by hardware or by a combination of hardware and software, the processor 502 may represent an entity (e.g., physically embodied in circuitry—in the form of processing circuitry 500) capable of performing operations according to example embodiments while configured accordingly. Thus, for example, when the processor 502 is embodied as an ASIC, FPGA or the like, the processor 502 may be specifically configured hardware for conducting the operations described herein. Alternatively, as another example, when the processor 502 is embodied as an executor of software instructions, the instructions may specifically configure the processor 502 to perform the operations described herein associated with testing functional PSA capabilities.

In an example embodiment, the processor 502 (or the processing circuitry 500) may be operably coupled to and control the operation of a PSA board 540 associated with each one of the test modules 410. In this regard, based on inputs received by the processing circuitry 500 responsive to insertion of a power unit into one of the cavities 412, the processing circuitry 500 may initiate the performance of testing via the PSA board 540 associated with the cavity 412. As such, in some embodiments, the processor 502 (or the processing circuitry 500) may be said to cause each of the operations described in connection with the PSA boards 540 in relation to generating/receiving and processing information associated with locking/unlocking the lock assembly 360 as described herein responsive to execution of instructions or algorithms configuring the processor 502 (or processing circuitry 500) accordingly.

In an exemplary embodiment, the memory 504 may include one or more non-transitory memory devices such as, for example, volatile and/or non-volatile memory that may be either fixed or removable. The memory 504 may be configured to store information, data, applications, instructions or the like for enabling the processing circuitry 500 to carry out various functions in accordance with exemplary embodiments of the present invention. For example, the memory 504 could be configured to buffer input data for processing by the processor 502. Additionally or alternatively, the memory 504 could be configured to store instructions for execution by the processor 502. As yet another alternative, the memory 504 may include one or more databases that may store a variety of data sets responsive to operation of the PSA boards 540. Among the contents of the memory 504, applications and/or instructions may be stored for execution by the processor 502 in order to carry out the functionality associated with each respective application/instruction. In some cases, the applications may include instructions for providing inputs to control operation of the PSA boards 540 as described herein.

In an example embodiment, the memory 504 may store data associated with signaling used for locking/unlocking the lock assembly 360 for analysis or debugging. Thus, for example, the memory 504 may store signaling parameters or characteristics that may be used to analyze why a particular test associated with a particular one of the devices 300 failed by comparing such parameters or characteristics to those associated with other devices that passed. The memory 504 may further store instructions for defining how to store testing information, how to aggregate or process such information, and/or how to represent such information on the monitor/display 520 or other output devices.

As shown in FIG. 5, the number of PSA boards 540 may match the number of testing modules 410 since each testing module 410 may include a corresponding PSA board 540. Each of the PSA boards 540 of an example embodiment may include an optical sensor 542 and an optical transmitter 544. However, it should be appreciated that to the extent audible signals are used, audio transmitters and receivers could replace the optical transmitter 544 and optical sensor 542, respectively. The optical transmitter 544 may be configured to transmit optical signals to the device 300 when inserted into one of the cavities 412, and the optical sensor 542 may be configured to receive optical signals or feedback from the device 300 in the cavity 412. In some cases, only the optical transmitter 544 may be employed, and the optical sensor 542 may be omitted.

Figure 6:
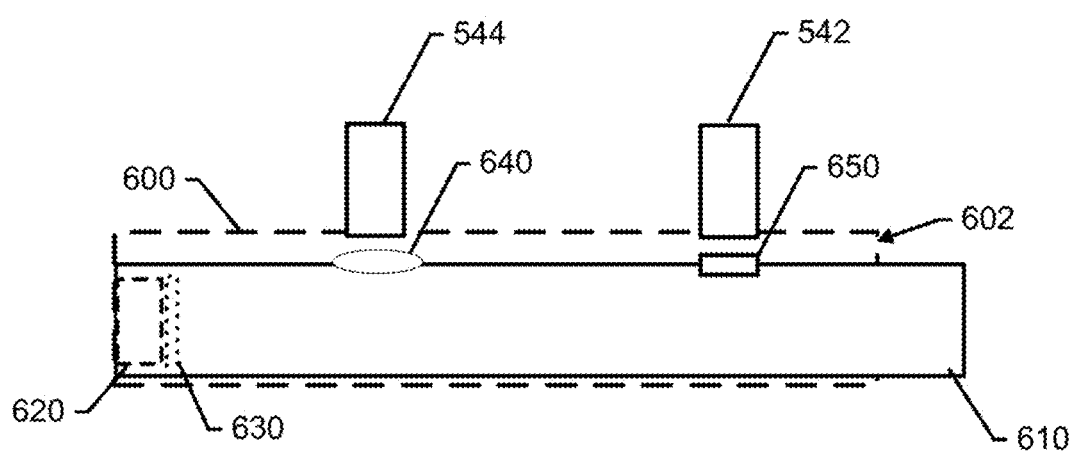
FIG. 6 is a side view of a cavity in a testing module in accordance with an example embodiment.

The optical transmitter 544 and optical sensor 542 (if employed) of each testing module 410 may be placed proximate to the cavity 412 of the corresponding testing module 410. FIG. 6 shows a side view (in partial cross section) of a cavity 600 (which is one example of the cavities 412 of FIG. 4) to illustrate how the optical transmitter 544 and the optical sensor 542 may be arranged in one example. The cavity 600 has an opening 602 at a proximal end thereof, and a distal end of the cavity 600 may be enclosed (e.g., within structures of the corresponding testing module 410). In this regard, FIG. 6 shows a power unit 610 of an instance of the device 300 inserted into the cavity 600 via the opening 602. Notably, a portion of the power unit 610 extends out of the cavity 600 (i.e., out of the opening 602) to enable the operator to manually remove the power unit 610 from the cavity 600 after testing is completed.

Upon insertion of the power unit 610 into the cavity 600, an electrical connection may be made between an electrical interface 620 (e.g., connection pins) located in the distal end of the cavity 600 and power pins 630 of the power unit 610. As noted above, the power unit 610 may have a unique ID associated therewith. In some example embodiments, the unique ID may automatically be read or extracted from the power unit 610 responsive to connection of the power pints 630 and the electrical interface 620. In some cases, insertion of the power unit 610 into the cavity 600, and the corresponding connection of the electrical interface 620 of the testing module 410 to the power pins 630 of the power unit 610 may also or alternatively automatically initiate a locking sequence to lock the power unit 610 (i.e., to lock the lock assembly 360). For example, the connection of the electrical interface 620 to the power pins 630 may trigger (e.g., via instruction by the PSA board 540 or the processor 502) the sending of a lock instruction to lock the lock assembly 360 via the connection. Although the power unit 610 may already be in a locked state, the provision of the lock instruction may ensure that regardless of the state of the power unit 610, the state is set to locked by default upon insertion of the power unit 610 into the cavity 600.

The insertion of the power unit 610 into the cavity 600 may also align the optical transmitter 544 with an aperture 640 formed in a body or housing of the power unit 610. An optical receiver of the power unit 610 may be aligned with the aperture 640 to receive optical signals transmitted by the optical transmitter 544. To the extent the optical sensor 542 is employed, the optical sensor 542 may also be aligned with a status light 650 of the power unit 610. The status light 650 may provide a pattern, color or other light output that may indicate status or status changes of the power unit 610.

In an example embodiment, the processing circuitry 500 may manage operation of the PSA board 540 (and more particularly of the optical transmitter 544 and the optical sensor 542) for the provision of an unlock instruction via the optical transmitter 544. For example, after the lock instruction is sent, a delay of a predetermined time may be initiated and, when expired, the optical transmitter 544 may provide an unlock code via optical signaling that comprises the unlock instruction delivered through the aperture 640 to an optical receiver of the power unit 610. If the unlock code is properly received by the power unit 610, the power unit 610 will switch to the lock assembly 360 to the unlocked state. Switching to the unlocked state may cause a feedback or status signal to be generated by the status light 650 of the power unit 610. The optical sensor 542 may detect the feedback or status signal from the status light 650 indicating the unlocking of the power unit 610.

Responsive to determining that the power unit 610 has been successfully transitioned to the unlocked state, the processing circuitry 500 may provide an indication to the status panel 414 and/or the display 440 to indicate that the functional test of the power unit 610 has passed (e.g., via a green light or other pass indication). The processing circuitry 500 may then further direct transitioning the power unit 610 back to the locked state (e.g., via the connection of the electrical interface 620 to the power pins 630 as described above). If the feedback or status signal from the status light 650 of the power unit 610 does not indicate that the power unit 610 successfully transitioned to the unlocked state, the processing circuitry 500 may provide an indication to the status panel 414 and/or the display 440 to indicate that the functional test of the power unit 610 has failed (e.g., via a red light or other fail indication).

FIG. 6 shows the optical transmitter 544 and the optical sensor 542 both disposed on a top portion of the cavity 600. However, the optical transmitter 544 and the optical sensor 542 could alternatively both be located on either side or the bottom portion of the cavity 600. Moreover, in some cases, the optical transmitter 544 and the optical sensor 542 could be on different sides of the cavity 600. For example, the optical transmitter 544 could be located at the top portion of the cavity 600 and the optical sensor 542 may be located at the bottom portion of the cavity 600. The structure of the power unit 610 (and location of the aperture 640 and status light 650) will typically dictate the locations of the optical transmitter 544 and the optical sensor 542 within the cavity 600. In some cases, the cavity 600 may also include one or more shielding structures (e.g., a wall or other physical separator) aimed at ensuring that the light signals transmitted by or to the optical transmitter 544 and the optical sensor 542 are not visible at the other one of the optical transmitter 544 or the optical sensor 542. In other words, the shielding structures may isolate each respective component from the other to avoid interference.

Although FIG. 6 illustrates the aperture 640 and the status light 650 being spaced apart from each other along the longitudinal length of the power unit 610, such spacing need not be provided in all cases. When such spacing exists, as noted above, the optical transmitter 544 and the optical sensor 542 may also be equally spaced apart along the longitudinal length of the cavity 600. As an alternative, the aperture 640 and status light 650 may be collocated or adjacent to each other. In such examples, the PSA board 700 of FIG. 7 may be employed.

Figure 7:
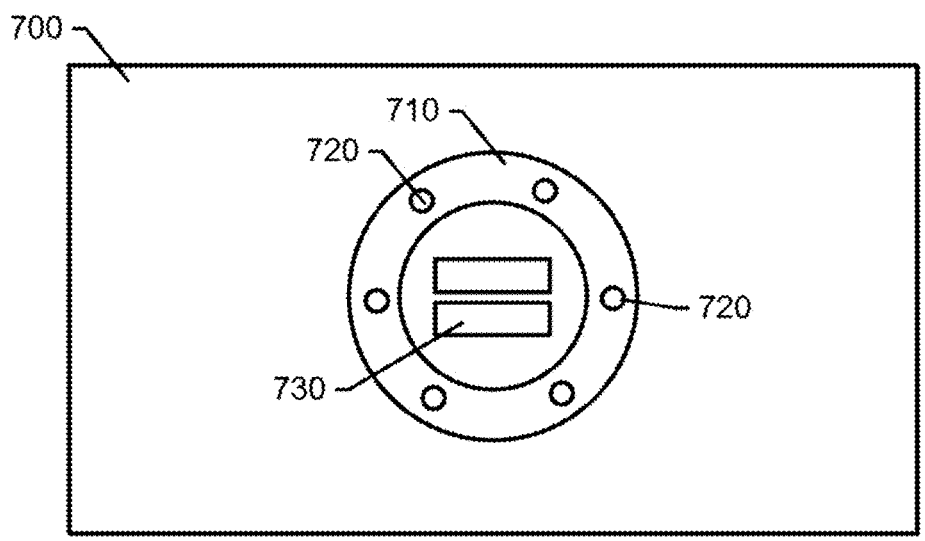
FIG. 7 is a diagram of a PSA board associated with an instance of the testing module in accordance with an example embodiment.

As shown in FIG. 7, the PSA board 700 may include a light ring 710 upon which a plurality of LEDs 720 may be placed. FIG. 7 shows six LEDs 720 provided on the light ring 710. However, more or fewer LEDs 720 could be included in alternative embodiments. The light ring 710 and the LEDs 720 may form the optical transmitter 544 of FIGS. 5 and 6. The PSA board 700 may also include a pair of phototransistors 730. However, a single phototransistor or multiple additional phototransistors may be employed in some alternatives. The phototransistors 730 may form the optical sensor 542. In this example, the light ring 710 surrounds the phototransistors 730. This supports a concentric collocation of the optical transmitter 544 and the optical sensor 542. However, other arrangements (e.g., adjacent) could alternatively be employed.

Some example embodiments may provide a test fixture that can be used to test aerosol provision devices prior to packaging, shipping or otherwise distributing such devices with respect to each devices ability to properly be unlocked using the PSA techniques defined for the devices. The test fixture may include a housing, a plurality of testing modules disposed at the housing where each of the testing modules includes a cavity configured to receive a portion of an aerosol provision device, and processing circuitry operably coupled to the testing modules. Each of the testing modules may be configured to interface with a lock assembly of a respective one of the aerosol provision devices to transition the lock assembly between a locked and unlocked state during a functional test controlled by the processing circuitry. The processing circuitry may be configured to conduct the functional test of at least two of the testing modules simultaneously. Notably, however, the lock assembly is just one example of an assembly that may be transitioned using the test fixture described above. Thus, more generally, the locked and unlocked states should be understood to be examples of transitions between an initial state and a transitioned state. Accordingly, as used herein, the terms locked state and unlocked state are examples of states between which the test fixture may be configured to transition one or more assemblies (such as the lock assembly). Other assemblies and other states may also be included in example embodiments without departing from the spirit and scope of the disclosure provided herein, and the corresponding claims.

The test fixture may include a number of modifications, augmentations, or optional additions, some of which are described herein. The modifications, augmentations or optional additions listed below may be added in any desirable combination. Within this context, the system as described above may be considered a first embodiment, and other embodiments may be defined by each respective combination of modifications, augmentations or optional additions. For example, a second embodiment may be defined in which the testing modules are removable and replaceable. The replacement of testing modules may be used to configure the testing modules for testing of different models of power units or aerosol provision devices by changing the shape of the cavity and positioning of the optical transmitter and/or optical sensor therein (among other possible changes). Alternatively or additionally, a third embodiment may be defined in which the cavity may be disposed at a front portion of the housing and extends longitudinally into the test fixture parallel to a surface on which the test fixture is supported. In an example embodiment, a fourth embodiment may be defined in which the cavity may be disposed at a top portion of the housing and extends longitudinally into the test fixture perpendicular to a surface on which the test fixture is supported. The fourth embodiment may be combined with any or all of embodiments one to two. In some examples, a fifth embodiment may be defined in which the processing circuitry may be configured to separately conduct and record testing for a power unit associated with each respective one of the testing modules. The fifth embodiment may be combined with any or all of embodiments one to four. In an example embodiment, a sixth embodiment may be defined in which the testing modules may each include a status panel configured to indicate a status of the functional test conducted at a corresponding one of the testing modules. The sixth embodiment may be combined with any or all of embodiments one to five. In some examples, a seventh embodiment may be defined in which the testing modules may each be operably coupled to a remote operator console, and the remote operator console may include a display configured to simultaneously indicate a status of the functional test being conducted at a plurality of the testing modules. The seventh embodiment may be combined with any or all of embodiments one to six. In an example embodiment, an eighth embodiment may be defined in which the processing circuitry may be configured to initiate the functional test based on operator instruction provided locally at a corresponding one of the testing modules. The eighth embodiment may be combined with any or all of embodiments one to seven. In some examples, a ninth embodiment may be defined in which the processing circuitry may be configured to initiate the functional test based on operator instruction provided remotely at an operator console operably coupled to the test fixture. The ninth embodiment may be combined with any or all of embodiments one to eight. In an example embodiment, a tenth embodiment may be defined in which the test fixture may be configured to receive a power unit of one of the aerosol provision devices in the cavity and the test fixture may be configured to determine a unique identifier associated with the power unit responsive to insertion of the power unit into the cavity. The tenth embodiment may be combined with any or all of embodiments one to nine. In some examples, an eleventh embodiment may be defined in which the processing circuitry may be configured to compare the unique identifier determined to a provided identifier to determine whether the provided identifier and the unique identifier determined match. The eleventh embodiment may be combined with any or all of embodiments one to ten. In some examples, a twelfth embodiment may be defined in which the processing circuitry may be configured to instruct a printer to print the unique identifier on a label responsive to determining that the provided identifier and the unique identifier determined match. The twelfth embodiment may be combined with any or all of embodiments one to eleven. In some examples, a thirteenth embodiment may be defined in which the test fixture may be configured to generate a unique code (e.g., a unique unlock code) based on the unique identifier, and the lock assembly may transition to the transitioned state (e.g., the unlocked state) responsive to receipt of the unique code. The thirteenth embodiment may be combined with any or all of embodiments one to twelve. In some examples, a fourteenth embodiment may be defined in which the test fixture may be configured to receive a power unit of one of the aerosol provision devices in the cavity, and each of the testing modules may include an optical transmitter and an optical sensor disposed at the cavity. The fourteenth embodiment may be combined with any or all of embodiments one to thirteen. In some examples, a fifteenth embodiment may be defined in which the processing circuitry may be configured to interface with the optical transmitter and the optical sensor to provide an optical code (e.g., an optical unlock code) to the power unit via the optical transmitter and receive feedback on a status of transitioning the assembly (e.g., unlocking the lock assembly) of the power unit via the optical sensor. The fifteenth embodiment may be combined with any or all of embodiments one to fourteen. In some examples, a sixteenth embodiment may be defined in which the optical transmitter and the optical sensor may be collocated within the cavity at a same side of the cavity and at a same longitudinal length along the cavity. The sixteenth embodiment may be combined with any or all of embodiments one to fifteen. In some examples, a seventeenth embodiment may be defined in which the optical sensor may include one or more phototransistors, and the optical transmitter may include a light ring and a plurality of light emitting diodes disposed around the light ring where the light ring extends around the one or more phototransistors. The seventeenth embodiment may be combined with any or all of embodiments one to sixteen. In some examples, an eighteenth embodiment may be defined in which the optical transmitter and the optical sensor may be located at different sides or longitudinal lengths within the cavity. The eighteenth embodiment may be combined with any or all of embodiments one to seventeen. In some examples, a nineteenth embodiment may be defined in which the optical transmitter of each respective one of the testing modules may be operated independently. The nineteenth embodiment may be combined with any or all of embodiments one to eighteen. In some examples, a twentieth embodiment may be defined in which the optical transmitter of the each respective one of the testing modules generates a different optical signal (e.g., optical unlock signal) into the cavity of the each respective one of the testing modules, and the different unlock signal is determined based on a unique identifier of the power unit. The twentieth embodiment may be combined with any or all of embodiments one to nineteen.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

The invention claimed is:

1. A fixture for functional control of an aerosol provision system, the fixture comprising:
    a housing;
    a module disposed at the housing, and including a cavity configured to receive a portion of the aerosol provision system; and
    processing circuitry operably coupled to the module,
    wherein the module is configured to interface with an assembly of the aerosol provision system to transition the assembly between an initial state and a transitioned state under control of the processing circuitry.

2. The fixture of claim 1, wherein the module is removable and replaceable.

3. The fixture of claim 1, wherein the cavity is disposed at a front portion of the housing and extends longitudinally into the fixture parallel to a surface on which the fixture is supported.

4. The fixture of claim 1, wherein the cavity is disposed at a top portion of the housing and extends longitudinally into the fixture perpendicular to a surface on which the fixture is supported.

5. The fixture of claim 1, wherein the module includes a status panel configured to indicate a status of the control conducted at the module.

6. The fixture of claim 1, wherein the module is operably coupled to a remote operator console that includes a display configured to indicate a status of the control being conducted at the module.

7. The fixture of claim 1, wherein the processing circuitry is configured to initiate the control based on operator instruction provided locally at the module.

8. The fixture of claim 1, wherein the processing circuitry is configured to initiate the control based on operator instruction provided remotely at an operator console operably coupled to the fixture.

9. The fixture of claim 1, wherein the aerosol provision system includes an aerosol provision device, and the fixture is configured to receive the aerosol provision device in the cavity, and
    wherein the fixture is configured to determine a unique identifier associated with the aerosol provision device responsive to insertion of the aerosol provision device into the cavity.

10. The fixture of claim 9, wherein the processing circuitry is configured to compare the unique identifier as determined to a provided identifier to determine whether the provided identifier and the unique identifier as determined match.

11. The fixture of claim 9, wherein the fixture is configured to generate a unique code based on the unique identifier, and
    wherein the assembly is configured to transition from the initial state to the transitioned state responsive to receipt of the unique code.

12. The fixture of claim 10, wherein the processing circuitry is configured to instruct a printer to print the unique identifier on a label responsive to a determination that the provided identifier and the unique identifier as determined match.

13. The fixture of claim 1, wherein the aerosol provision system includes an aerosol provision device, and the fixture is configured to receive the aerosol provision device in the cavity, and
    wherein the module comprises an optical transmitter and an optical sensor disposed at the cavity.

14. The fixture of claim 13, wherein the processing circuitry is configured to interface with the optical transmitter to provide an optical code to the aerosol provision device via the optical transmitter, and interface with the optical sensor to receive feedback on a status of transitioning the assembly between the initial state and the transitioned state of the aerosol provision device via the optical sensor.

15. The fixture of claim 13, wherein the optical transmitter and the optical sensor are collocated within the cavity at a same side of the cavity and at a same longitudinal length along the cavity.

16. The fixture of claim 13, wherein the optical transmitter and the optical sensor are located at different sides or longitudinal lengths within the cavity.

17. The fixture of claim 13, wherein the optical transmitter of the module is configured to transmit an optical signal into the cavity of the module, and the optical signal is determined based on a unique identifier of the aerosol provision device.

18. The fixture of claim 15, wherein the optical sensor comprises one or more phototransistors, and
    wherein the optical transmitter comprises a light ring and a plurality of light emitting diodes disposed around the light ring, the light ring extending around the one or more phototransistors.

* * * * *